US010674944B2

(12) United States Patent
Pace

(10) Patent No.: US 10,674,944 B2
(45) Date of Patent: Jun. 9, 2020

(54) COMPACT MEDICAL DEVICE INSERTERS AND RELATED SYSTEMS AND METHODS

(71) Applicant: ABBOTT DIABETES CARE INC., Alameda, CA (US)

(72) Inventor: Louis G. Pace, San Carlos, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 836 days.

(21) Appl. No.: 15/154,736

(22) Filed: May 13, 2016

(65) Prior Publication Data

US 2016/0331284 A1 Nov. 17, 2016

Related U.S. Application Data

(60) Provisional application No. 62/161,787, filed on May 14, 2015.

(51) Int. Cl.
*A61B 5/145* (2006.01)
*A61M 5/158* (2006.01)
(Continued)

(52) U.S. Cl.
CPC ...... *A61B 5/14503* (2013.01); *A61B 5/14532* (2013.01); *A61M 5/158* (2013.01);
(Continued)

(58) Field of Classification Search
CPC .............. A61B 5/14503; A61B 5/6832; A61B 5/14532; A61B 2560/063; A61B 5/1451; A61B 5/14546; A61B 5/0022; A61M 5/158; A61M 5/14244; A61M 2005/1585; A61M 5/1723
See application file for complete search history.

(56) References Cited

U.S. PATENT DOCUMENTS 3,132,123 A 5/1964 Harris, Jr. et al.
3,260,656 A 7/1966 Ross, Jr.
(Continued)

FOREIGN PATENT DOCUMENTS

CN 1202872 5/2005
EP 0320109 6/1989
(Continued)

OTHER PUBLICATIONS

EP, 16793637.6 Extended Search Report, dated Oct. 9, 2018.
(Continued)

*Primary Examiner* — Jacqueline Cheng
*Assistant Examiner* — Tho Q Tran
(74) *Attorney, Agent, or Firm* — One LLP

(57) ABSTRACT

Compact medical device inserters, systems incorporating the same, and related methods of use are described. The inserters can include a housing, a sharp support, a sharp body, and a shroud, and can apply a sensor control device to a recipient with a sensor implanted in the recipient's body. The shroud can extend from the sensor control device in a position that covers or protects the sensor and a sharp, and can be retracted by pressure placed upon the inserter against the recipient's body to cause the sharp and sensor to penetrate the body, after which the sharp can be automatically withdrawn with the aid of a biasing element.

18 Claims, 15 Drawing Sheets

(51) Int. Cl.
  *A61B 5/00* (2006.01)
  *A61M 5/172* (2006.01)
  *A61M 5/142* (2006.01)

(52) U.S. Cl.
  CPC .......... *A61B 5/0022* (2013.01); *A61B 5/1451* (2013.01); *A61B 5/14546* (2013.01); *A61B 2560/063* (2013.01); *A61M 5/14244* (2013.01); *A61M 5/1723* (2013.01); *A61M 2005/1585* (2013.01)

(56) References Cited

U.S. PATENT DOCUMENTS

| | | |
|---|---|---|
| 3,522,807 A | 8/1970 | Millenbach |
| 3,581,062 A | 5/1971 | Aston |
| 3,653,841 A | 4/1972 | Klein |
| 3,670,727 A | 6/1972 | Reiterman |
| 3,719,564 A | 3/1973 | Lilly, Jr. et al. |
| 3,776,832 A | 12/1973 | Oswin et al. |
| 3,837,339 A | 9/1974 | Aisenberg et al. |
| 3,926,760 A | 12/1975 | Allen et al. |
| 3,949,388 A | 4/1976 | Fuller |
| 3,972,320 A | 8/1976 | Kalman |
| 3,979,274 A | 9/1976 | Newman |
| 4,008,717 A | 2/1977 | Kowarski |
| 4,016,866 A | 4/1977 | Lawton |
| 4,036,749 A | 7/1977 | Anderson |
| 4,055,175 A | 10/1977 | Clemens et al. |
| 4,059,406 A | 11/1977 | Fleet |
| 4,076,596 A | 2/1978 | Connery et al. |
| 4,098,574 A | 7/1978 | Dappen |
| 4,100,048 A | 7/1978 | Pompei et al. |
| 4,120,292 A | 10/1978 | LeBlanc, Jr. et al. |
| 4,129,128 A | 12/1978 | McFarlane |
| 4,151,845 A | 5/1979 | Clemens |
| 4,168,205 A | 9/1979 | Danniger et al. |
| 4,172,770 A | 10/1979 | Semersky et al. |
| 4,178,916 A | 12/1979 | McNamara |
| 4,206,755 A | 6/1980 | Klein |
| 4,224,125 A | 9/1980 | Nakamura et al. |
| 4,240,438 A | 12/1980 | Updike et al. |
| 4,245,634 A | 1/1981 | Albisser et al. |
| 4,247,297 A | 1/1981 | Berti et al. |
| 4,294,258 A | 10/1981 | Bernard |
| 4,327,725 A | 5/1982 | Cortese et al. |
| 4,340,458 A | 7/1982 | Lerner et al. |
| 4,344,438 A | 8/1982 | Schultz |
| 4,349,728 A | 9/1982 | Phillips et al. |
| 4,352,960 A | 10/1982 | Dormer et al. |
| 4,353,888 A | 10/1982 | Sefton |
| 4,356,074 A | 10/1982 | Johnson |
| 4,365,637 A | 12/1982 | Johnson |
| 4,366,033 A | 12/1982 | Richter et al. |
| 4,373,527 A | 2/1983 | Fischell |
| 4,375,399 A | 3/1983 | Havas et al. |
| 4,384,586 A | 5/1983 | Christiansen |
| 4,390,621 A | 6/1983 | Bauer |
| 4,401,122 A | 8/1983 | Clark, Jr. |
| 4,404,066 A | 9/1983 | Johnson |
| 4,418,148 A | 11/1983 | Oberhardt |
| 4,425,920 A | 1/1984 | Bourland et al. |
| 4,427,004 A | 1/1984 | Miller et al. |
| 4,427,770 A | 1/1984 | Chen et al. |
| 4,431,004 A | 2/1984 | Bessman et al. |
| 4,436,094 A | 3/1984 | Cerami |
| 4,440,175 A | 4/1984 | Wilkins |
| 4,450,842 A | 5/1984 | Zick et al. |
| 4,458,686 A | 7/1984 | Clark, Jr. |
| 4,461,691 A | 7/1984 | Frank |
| 4,469,110 A | 9/1984 | Slama |
| 4,477,314 A | 10/1984 | Richter et al. |
| 4,478,976 A | 10/1984 | Goertz et al. |
| 4,484,987 A | 11/1984 | Gough |
| 4,494,950 A | 1/1985 | Fischell |
| 4,509,531 A | 4/1985 | Ward |
| 4,522,690 A | 6/1985 | Venkatsetty |
| 4,524,114 A | 6/1985 | Samuels et al. |
| 4,526,661 A | 7/1985 | Steckhan et al. |
| 4,527,240 A | 7/1985 | Kvitash |
| 4,534,356 A | 8/1985 | Papadakis |
| 4,538,616 A | 9/1985 | Rogoff |
| 4,543,955 A | 10/1985 | Schroeppel |
| 4,545,382 A | 10/1985 | Higgins et al. |
| 4,552,840 A | 11/1985 | Riffer |
| 4,560,534 A | 12/1985 | Kung et al. |
| 4,571,292 A | 2/1986 | Liu et al. |
| 4,573,994 A | 3/1986 | Fischell et al. |
| 4,581,336 A | 4/1986 | Malloy et al. |
| 4,595,011 A | 6/1986 | Phillips |
| 4,619,754 A | 10/1986 | Niki et al. |
| 4,619,793 A | 10/1986 | Lee |
| 4,627,445 A | 12/1986 | Garcia et al. |
| 4,627,842 A | 12/1986 | Katz |
| 4,627,908 A | 12/1986 | Miller |
| 4,633,878 A | 1/1987 | Bombardien |
| 4,637,403 A | 1/1987 | Garcia et al. |
| 4,650,547 A | 3/1987 | Gough |
| 4,654,197 A | 3/1987 | Lilja et al. |
| 4,655,880 A | 4/1987 | Liu |
| 4,655,885 A | 4/1987 | Hill et al. |
| 4,663,824 A | 5/1987 | Kenmochi |
| 4,671,288 A | 6/1987 | Gough |
| 4,679,562 A | 7/1987 | Luksha |
| 4,680,268 A | 7/1987 | Clark, Jr. |
| 4,682,602 A | 7/1987 | Prohaska |
| 4,684,537 A | 8/1987 | Graetzel et al. |
| 4,685,463 A | 8/1987 | Williams |
| 4,685,466 A | 8/1987 | Rau |
| 4,698,057 A | 10/1987 | Joishy |
| 4,703,756 A | 11/1987 | Gough et al. |
| 4,711,245 A | 12/1987 | Higgins et al. |
| 4,711,247 A | 12/1987 | Fishman |
| 4,717,673 A | 1/1988 | Wrighton et al. |
| 4,721,601 A | 1/1988 | Wrighton et al. |
| 4,721,677 A | 1/1988 | Clark, Jr. |
| 4,726,378 A | 2/1988 | Kaplan |
| 4,726,716 A | 2/1988 | McGuire |
| 4,729,672 A | 3/1988 | Takagi |
| 4,731,726 A | 3/1988 | Allen, III |
| 4,749,985 A | 6/1988 | Corsberg |
| 4,755,173 A | 7/1988 | Konopka |
| 4,758,323 A | 7/1988 | Davis et al. |
| 4,759,371 A | 7/1988 | Franetzki |
| 4,759,828 A | 7/1988 | Young et al. |
| 4,764,416 A | 8/1988 | Ueyama et al. |
| 4,776,944 A | 10/1988 | Janata et al. |
| 4,777,953 A | 10/1988 | Ash et al. |
| 4,779,618 A | 10/1988 | Gough |
| 4,781,683 A | 11/1988 | Wozniak et al. |
| 4,781,798 A | 11/1988 | Gough |
| 4,784,736 A | 11/1988 | Lonsdale et al. |
| 4,795,707 A | 1/1989 | Niiyama et al. |
| 4,796,634 A | 1/1989 | Huntsman et al. |
| 4,805,624 A | 2/1989 | Yao et al. |
| 4,813,424 A | 3/1989 | Wilkins |
| 4,815,469 A | 3/1989 | Cohen et al. |
| 4,820,399 A | 4/1989 | Senda et al. |
| 4,822,337 A | 4/1989 | Newhouse et al. |
| 4,830,959 A | 5/1989 | McNeil et al. |
| 4,832,797 A | 5/1989 | Vadgama et al. |
| RE32,947 E | 6/1989 | Dormer et al. |
| 4,840,893 A | 6/1989 | Hill et al. |
| 4,848,351 A | 7/1989 | Finch |
| 4,854,322 A | 8/1989 | Ash et al. |
| 4,871,351 A | 10/1989 | Feingold |
| 4,871,440 A | 10/1989 | Nagata et al. |
| 4,874,500 A | 10/1989 | Madou et al. |
| 4,890,622 A | 1/1990 | Gough |
| 4,894,137 A | 1/1990 | Takizawa et al. |
| 4,895,147 A | 1/1990 | Bodicky et al. |
| 4,897,162 A | 1/1990 | Lewandowski et al. |
| 4,897,173 A | 1/1990 | Nankai et al. |
| 4,909,908 A | 3/1990 | Ross et al. |
| 4,911,794 A | 3/1990 | Parce et al. |

(56) References Cited

U.S. PATENT DOCUMENTS

| | | |
|---|---|---|
| 4,917,800 A | 4/1990 | Lonsdale et al. |
| 4,919,141 A | 4/1990 | Zier et al. |
| 4,919,767 A | 4/1990 | Vadgama et al. |
| 4,921,199 A | 5/1990 | Villavecs |
| 4,923,586 A | 5/1990 | Katayama et al. |
| 4,925,268 A | 5/1990 | Iyer et al. |
| 4,927,516 A | 5/1990 | Yamaguchi et al. |
| 4,934,369 A | 6/1990 | Maxwell |
| 4,935,105 A | 6/1990 | Churchouse |
| 4,935,345 A | 6/1990 | Guibeau et al. |
| 4,938,860 A | 7/1990 | Wogoman |
| 4,944,299 A | 7/1990 | Silvian |
| 4,950,378 A | 8/1990 | Nagara |
| 4,953,552 A | 9/1990 | DeMarzo |
| 4,954,129 A | 9/1990 | Giuliani et al. |
| 4,969,468 A | 11/1990 | Byers et al. |
| 4,970,145 A | 11/1990 | Bennetto et al. |
| 4,974,929 A | 12/1990 | Curry |
| 4,986,271 A | 1/1991 | Wilkins |
| 4,988,341 A | 1/1991 | Columbus et al. |
| 4,994,167 A | 2/1991 | Shults et al. |
| 4,995,402 A | 2/1991 | Smith et al. |
| 5,000,180 A | 3/1991 | Kuypers et al. |
| 5,001,054 A | 3/1991 | Wagner |
| 5,013,161 A | 5/1991 | Zaragoza et al. |
| 5,019,974 A | 5/1991 | Beckers |
| 5,035,860 A | 7/1991 | Kleingeld et al. |
| 5,036,860 A | 8/1991 | Leigh et al. |
| 5,047,044 A | 9/1991 | Smith et al. |
| 5,050,612 A | 9/1991 | Matsumura |
| 5,055,171 A | 10/1991 | Peck |
| 5,058,592 A | 10/1991 | Whisler |
| 5,070,535 A | 12/1991 | Hochmair et al. |
| 5,082,550 A | 1/1992 | Rishpon et al. |
| 5,082,786 A | 1/1992 | Nakamoto |
| 5,089,112 A | 2/1992 | Skotheim et al. |
| 5,095,904 A | 3/1992 | Seligman et al. |
| 5,101,814 A | 4/1992 | Palti |
| 5,106,365 A | 4/1992 | Hernandez |
| 5,108,564 A | 4/1992 | Szuminsky et al. |
| 5,108,889 A | 4/1992 | Smith et al. |
| 5,109,850 A | 5/1992 | Blanco et al. |
| 5,120,420 A | 6/1992 | Nankai et al. |
| 5,122,925 A | 6/1992 | Inpyn |
| 5,126,034 A | 6/1992 | Carter et al. |
| 5,133,856 A | 7/1992 | Yamaguchi et al. |
| 5,135,003 A | 8/1992 | Souma |
| 5,140,985 A | 8/1992 | Schroeder et al. |
| 5,141,868 A | 8/1992 | Shanks et al. |
| 5,161,532 A | 11/1992 | Joseph |
| 5,165,407 A | 11/1992 | Wilson et al. |
| 5,174,291 A | 12/1992 | Schoonen et al. |
| 5,190,041 A | 3/1993 | Palti |
| 5,192,416 A | 3/1993 | Wang et al. |
| 5,198,367 A | 3/1993 | Aizawa et al. |
| 5,202,261 A | 4/1993 | Musho et al. |
| 5,205,920 A | 4/1993 | Oyama et al. |
| 5,208,154 A | 5/1993 | Weaver et al. |
| 5,209,229 A | 5/1993 | Gilli |
| 5,217,595 A | 6/1993 | Smith et al. |
| 5,229,282 A | 7/1993 | Yoshioka et al. |
| 5,234,835 A | 8/1993 | Nestor et al. |
| 5,238,729 A | 8/1993 | Debe |
| 5,246,867 A | 9/1993 | Lakowicz et al. |
| 5,250,439 A | 10/1993 | Musho et al. |
| 5,262,035 A | 11/1993 | Gregg et al. |
| 5,262,305 A | 11/1993 | Heller et al. |
| 5,264,103 A | 11/1993 | Yoshioka et al. |
| 5,264,104 A | 11/1993 | Gregg et al. |
| 5,264,105 A | 11/1993 | Gregg et al. |
| 5,264,106 A | 11/1993 | McAleer et al. |
| 5,271,815 A | 12/1993 | Wong |
| 5,279,294 A | 1/1994 | Anderson |
| 5,284,156 A | 2/1994 | Schramm et al. |
| 5,285,792 A | 2/1994 | Sjoquist et al. |
| 5,286,362 A | 2/1994 | Hoenes et al. |
| 5,286,364 A | 2/1994 | Yacynych et al. |
| 5,288,636 A | 2/1994 | Pollmann et al. |
| 5,293,546 A | 3/1994 | Tadros et al. |
| 5,293,877 A | 3/1994 | O'Hara et al. |
| 5,299,571 A | 4/1994 | Mastrototaro |
| 5,320,098 A | 6/1994 | Davidson |
| 5,320,725 A | 6/1994 | Gregg et al. |
| 5,322,063 A | 6/1994 | Allen et al. |
| 5,337,747 A | 8/1994 | Neftei |
| 5,340,722 A | 8/1994 | Wolfbeis et al. |
| 5,342,789 A | 8/1994 | Chick et al. |
| 5,352,348 A | 10/1994 | Young et al. |
| 5,356,786 A | 10/1994 | Heller et al. |
| 5,360,404 A | 11/1994 | Novacek et al. |
| 5,368,028 A | 11/1994 | Palti |
| 5,372,133 A | 12/1994 | Hogen Esch |
| 5,372,427 A | 12/1994 | Padovani et al. |
| 5,376,251 A | 12/1994 | Kaneko et al. |
| 5,378,628 A | 1/1995 | Gratzel et al. |
| 5,379,238 A | 1/1995 | Stark |
| 5,387,327 A | 2/1995 | Khan |
| 5,390,671 A | 2/1995 | Lord et al. |
| 5,391,250 A | 2/1995 | Cheney, II et al. |
| 5,395,504 A | 3/1995 | Saurer et al. |
| 5,400,782 A | 3/1995 | Beaubiah |
| 5,408,999 A | 4/1995 | Singh et al. |
| 5,411,647 A | 5/1995 | Johnson et al. |
| 5,425,361 A | 6/1995 | Fenzlein et al. |
| 5,431,160 A | 7/1995 | Wilkins |
| 5,431,921 A | 7/1995 | Thombre |
| 5,437,999 A | 8/1995 | Dieboid et al. |
| 5,462,645 A | 10/1995 | Albery et al. |
| 5,469,846 A | 11/1995 | Khan |
| 5,472,317 A | 12/1995 | Field et al. |
| 5,489,414 A | 2/1996 | Schreiber et al. |
| 5,491,474 A | 2/1996 | Suni et al. |
| 5,494,562 A | 2/1996 | Maley et al. |
| 5,496,453 A | 3/1996 | Uenoyama et al. |
| 5,497,772 A | 3/1996 | Schulman et al. |
| 5,507,288 A | 4/1996 | Bocker et al. |
| 5,509,410 A | 4/1996 | Hill et al. |
| 5,514,718 A | 5/1996 | Lewis et al. |
| 5,527,288 A | 6/1996 | Gross et al. |
| 5,531,878 A | 7/1996 | Vadgama et al. |
| 5,545,191 A | 8/1996 | Mann et al. |
| 5,549,368 A | 8/1996 | Shields |
| 5,551,427 A | 9/1996 | Altman |
| 5,560,357 A | 10/1996 | Faupei et al. |
| 5,562,713 A | 10/1996 | Silvian |
| 5,565,085 A | 10/1996 | Ikeda et al. |
| 5,567,302 A | 10/1996 | Song et al. |
| 5,568,806 A | 10/1996 | Cheney, II et al. |
| 5,569,186 A | 10/1996 | Lord et al. |
| 5,575,563 A | 11/1996 | Chiu et al. |
| 5,582,184 A | 12/1996 | Erickson et al. |
| 5,582,697 A | 12/1996 | Ikeda et al. |
| 5,582,698 A | 12/1996 | Flaherty et al. |
| 5,584,813 A | 12/1996 | Livingston et al. |
| 5,586,553 A | 12/1996 | Halli et al. |
| 5,589,326 A | 12/1996 | Deng et al. |
| 5,593,852 A | 1/1997 | Heller et al. |
| 5,596,150 A | 1/1997 | Arndt et al. |
| 5,601,435 A | 2/1997 | Quy |
| 5,609,575 A | 3/1997 | Larson et al. |
| 5,613,978 A | 3/1997 | Harding |
| 5,617,851 A | 4/1997 | Lipkovker |
| 5,628,310 A | 5/1997 | Rao et al. |
| 5,628,890 A | 5/1997 | Carter et al. |
| 5,632,557 A | 5/1997 | Simons |
| 5,638,832 A | 6/1997 | Singer et al. |
| 5,640,954 A | 6/1997 | Pfeiffer et al. |
| 5,651,869 A | 7/1997 | Yoshioka et al. |
| 5,653,239 A | 8/1997 | Pompei et al. |
| 5,660,163 A | 8/1997 | Schulman et al. |
| 5,665,071 A | 9/1997 | Wyrick |
| 5,665,222 A | 9/1997 | Heller et al. |
| 5,670,031 A | 9/1997 | Hintsche et al. |
| 5,680,858 A | 10/1997 | Hansen et al. |

(56) References Cited

U.S. PATENT DOCUMENTS

| | | |
|---|---|---|
| 5,682,233 A | 10/1997 | Brinda |
| 5,695,623 A | 12/1997 | Michel et al. |
| 5,708,247 A | 1/1998 | McAleer et al. |
| 5,711,001 A | 1/1998 | Bussan et al. |
| 5,711,297 A | 1/1998 | Iliff et al. |
| 5,711,861 A | 1/1998 | Ward et al. |
| 5,711,862 A | 1/1998 | Sakoda et al. |
| 5,733,044 A | 3/1998 | Rose et al. |
| 5,735,285 A | 4/1998 | Albert et al. |
| 5,741,211 A | 4/1998 | Renirie et al. |
| 5,749,656 A | 5/1998 | Boehm et al. |
| 5,766,131 A | 6/1998 | Kondo et al. |
| 5,771,001 A | 6/1998 | Cobb |
| 5,772,586 A | 6/1998 | Heinonen et al. |
| 5,779,665 A | 7/1998 | Mastrototaro et al. |
| 5,791,344 A | 8/1998 | Schulman et al. |
| 5,800,420 A | 9/1998 | Gross et al. |
| 5,807,375 A | 9/1998 | Gross et al. |
| 5,814,020 A | 9/1998 | Gross |
| 5,820,551 A | 10/1998 | Hill et al. |
| 5,820,622 A | 10/1998 | Gross et al. |
| 5,822,715 A | 10/1998 | Worthington et al. |
| 5,827,184 A | 10/1998 | Netherly et al. |
| 5,840,020 A | 11/1998 | Heinonen et al. |
| 5,842,983 A | 12/1998 | Abel et al. |
| 5,851,197 A | 12/1998 | Marano et al. |
| 5,858,001 A | 1/1999 | Tsals et al. |
| 5,865,804 A | 2/1999 | Bachynsky |
| 5,885,211 A | 3/1999 | Eppstein et al. |
| 5,899,855 A | 5/1999 | Brown |
| 5,924,979 A | 7/1999 | Sedlow et al. |
| 5,925,021 A | 7/1999 | Castellano et al. |
| 5,931,814 A | 8/1999 | Alex et al. |
| 5,948,006 A | 9/1999 | Mann |
| 5,951,521 A | 9/1999 | Mastrototaro et al. |
| 5,954,643 A | 9/1999 | Van Antwerp |
| 5,954,685 A | 9/1999 | Tierny |
| 5,957,854 A | 9/1999 | Besson et al. |
| 5,961,451 A | 10/1999 | Reber et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,972,199 A | 10/1999 | Heller et al. |
| 5,987,353 A | 11/1999 | Khatchatrian et al. |
| 5,993,411 A | 11/1999 | Choi |
| 5,995,860 A | 11/1999 | Sun et al. |
| 5,997,501 A | 12/1999 | Gross et al. |
| 6,001,067 A | 12/1999 | Shults et al. |
| 6,004,278 A | 12/1999 | Botich et al. |
| 6,017,335 A | 1/2000 | Burnham |
| 6,022,368 A | 2/2000 | Gavronsky et al. |
| 6,024,699 A | 2/2000 | Surwit et al. |
| 6,026,321 A | 2/2000 | Miyata et al. |
| 6,027,459 A | 2/2000 | Shain et al. |
| 6,049,727 A | 4/2000 | Crothall |
| 6,056,718 A | 5/2000 | Funderburk et al. |
| 6,068,399 A | 5/2000 | Tseng |
| 6,083,710 A | 7/2000 | Heller et al. |
| 6,088,608 A | 7/2000 | Schulman et al. |
| 6,091,975 A | 7/2000 | Daddona et al. |
| 6,091,976 A | 7/2000 | Pfeiffer et al. |
| 6,093,172 A | 7/2000 | Funderbunk et al. |
| 6,102,896 A | 8/2000 | Roser |
| 6,103,033 A | 8/2000 | Say et al. |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,134,461 A | 10/2000 | Say et al. |
| 6,143,164 A | 11/2000 | Heller et al. |
| 6,159,147 A | 12/2000 | Lichter et al. |
| 6,162,611 A | 12/2000 | Heller et al. |
| 6,175,752 B1 | 1/2001 | Say et al. |
| 6,186,982 B1 | 2/2001 | Gross et al. |
| 6,200,265 B1 | 3/2001 | Walsh et al. |
| 6,212,416 B1 | 4/2001 | Ward et al. |
| 6,219,574 B1 | 4/2001 | Cormier et al. |
| 6,248,067 B1 | 6/2001 | Causey, III et al. |
| 6,254,536 B1 | 7/2001 | DeVito |
| 6,254,586 B1 | 7/2001 | Mann et al. |
| 6,275,717 B1 | 8/2001 | Gross et al. |
| 6,283,761 B1 | 9/2001 | Joao |
| 6,283,982 B1 | 9/2001 | Levaughn et al. |
| 6,284,478 B1 | 9/2001 | Heller et al. |
| 6,293,925 B1 | 9/2001 | Safabash et al. |
| 6,295,506 B1 | 9/2001 | Heinonen et al. |
| 6,306,104 B1 | 10/2001 | Cunningham et al. |
| 6,309,884 B1 | 10/2001 | Cooper et al. |
| 6,329,161 B1 | 12/2001 | Heller et al. |
| 6,331,244 B1 | 12/2001 | Lewis et al. |
| 6,338,790 B1 | 1/2002 | Feldman et al. |
| 6,348,640 B1 | 2/2002 | Navot et al. |
| 6,359,444 B1 | 3/2002 | Grimes |
| 6,360,888 B1 | 3/2002 | McIvor et al. |
| 6,368,141 B1 | 4/2002 | Van Antwerp et al. |
| 6,368,274 B1 | 4/2002 | Van Antwerp et al. |
| 6,377,828 B1 | 4/2002 | Chaiken et al. |
| 6,379,301 B1 | 4/2002 | Worthington et al. |
| 6,409,740 B1 | 6/2002 | Kuhr et al. |
| 6,413,393 B1 | 7/2002 | Van Antwerp et al. |
| 6,418,332 B1 | 7/2002 | Mastrototaro et al. |
| 6,424,847 B1 | 7/2002 | Mastrototaro et al. |
| 6,427,088 B1 | 7/2002 | Bowman, IV et al. |
| 6,437,679 B1 | 8/2002 | Rogues |
| 6,440,068 B1 | 8/2002 | Brown et al. |
| 6,445,374 B2 | 9/2002 | Albert et al. |
| 6,478,736 B1 | 11/2002 | Mault |
| 6,482,176 B1 | 11/2002 | Wich |
| 6,484,045 B1 | 11/2002 | Holker et al. |
| 6,484,046 B1 | 11/2002 | Say et al. |
| 6,514,718 B2 | 2/2003 | Heller et al. |
| 6,520,326 B2 | 2/2003 | McIvor et al. |
| 6,522,927 B1 | 2/2003 | Bishay et al. |
| 6,551,494 B1 | 4/2003 | Heller et al. |
| 6,554,798 B1 | 4/2003 | Mann et al. |
| 6,558,320 B1 | 5/2003 | Causey, III et al. |
| 6,558,321 B1 | 5/2003 | Burd et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,572,566 B2 | 6/2003 | Effenhauser |
| 6,576,101 B1 | 6/2003 | Heller et al. |
| 6,577,899 B2 | 6/2003 | Lebel et al. |
| 6,579,690 B1 | 6/2003 | Bonnecaze et al. |
| 6,585,644 B2 | 7/2003 | Lebel et al. |
| 6,589,229 B1 | 7/2003 | Connelly et al. |
| 6,591,125 B1 | 7/2003 | Buse et al. |
| 6,595,919 B2 | 7/2003 | Berner et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,610,012 B2 | 8/2003 | Mault |
| 6,613,015 B2 | 9/2003 | Sandstrom et al. |
| 6,633,772 B2 | 10/2003 | Ford et al. |
| 6,635,014 B2 | 10/2003 | Starkweather et al. |
| 6,648,821 B2 | 11/2003 | Lebel et al. |
| 6,654,625 B1 | 11/2003 | Say et al. |
| 6,659,948 B2 | 12/2003 | Lebel et al. |
| 6,666,849 B1 | 12/2003 | Marshall et al. |
| 6,668,196 B1 | 12/2003 | Villegas et al. |
| 6,675,030 B2 | 1/2004 | Ciurczak et al. |
| 6,676,290 B1 | 1/2004 | Lu |
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,702,857 B2 | 3/2004 | Brauker et al. |
| 6,733,446 B2 | 5/2004 | Lebel et al. |
| 6,740,075 B2 | 5/2004 | Lebel et al. |

(56) References Cited

U.S. PATENT DOCUMENTS

| | | |
|---|---|---|
| 6,741,877 B1 | 5/2004 | Shults et al. |
| 6,746,582 B2 | 6/2004 | Heller et al. |
| 6,758,810 B2 | 7/2004 | Lebel et al. |
| 6,770,030 B1 | 8/2004 | Schaupp et al. |
| 6,790,178 B1 | 9/2004 | Mault et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,830,551 B1 | 12/2004 | Uchigaki et al. |
| 6,837,858 B2 | 1/2005 | Cunningham et al. |
| 6,837,885 B2 | 1/2005 | Koblish et al. |
| 6,837,988 B2 | 1/2005 | Leong et al. |
| 6,849,052 B2 | 2/2005 | Uchigaki et al. |
| 6,854,882 B2 | 2/2005 | Chen |
| 6,862,465 B2 | 3/2005 | Shults et al. |
| 6,873,268 B2 | 3/2005 | Lebel et al. |
| 6,881,551 B2 | 4/2005 | Heller et al. |
| 6,892,085 B2 | 5/2005 | McIvor et al. |
| 6,895,265 B2 | 5/2005 | Silver |
| 6,931,327 B2 | 8/2005 | Goode, Jr. et al. |
| 6,932,894 B2 | 8/2005 | Mao et al. |
| 6,936,006 B2 | 8/2005 | Sabra |
| 6,942,518 B2 | 9/2005 | Liamos et al. |
| 6,950,708 B2 | 9/2005 | Bowman, IV et al. |
| 6,958,705 B2 | 10/2005 | Lebel et al. |
| 6,959,211 B2 | 10/2005 | Rule et al. |
| 6,968,294 B2 | 11/2005 | Gutta et al. |
| 6,971,274 B2 | 12/2005 | Olin |
| 6,971,999 B2 | 12/2005 | Py et al. |
| 6,974,437 B2 | 12/2005 | Lebel et al. |
| 6,990,366 B2 | 1/2006 | Say et al. |
| 6,997,907 B2 | 2/2006 | Safabash et al. |
| 6,998,247 B2 | 2/2006 | Monfre et al. |
| 7,003,336 B2 | 2/2006 | Holker et al. |
| 7,003,340 B2 | 2/2006 | Say et al. |
| 7,003,341 B2 | 2/2006 | Say et al. |
| 7,005,857 B2 | 2/2006 | Stiene et al. |
| 7,024,245 B2 | 4/2006 | Lebel et al. |
| 7,025,743 B2 | 4/2006 | Mann et al. |
| 7,041,068 B2 | 5/2006 | Freeman et al. |
| 7,041,468 B2 | 5/2006 | Drucker et al. |
| 7,052,483 B2 | 5/2006 | Wojcik |
| 7,056,302 B2 | 6/2006 | Douglas |
| 7,074,307 B2 | 7/2006 | Simpson et al. |
| 7,081,195 B2 | 7/2006 | Simpson et al. |
| 7,097,637 B2 | 8/2006 | Triplett et al. |
| 7,098,803 B2 | 8/2006 | Mann et al. |
| 7,108,778 B2 | 9/2006 | Simpson et al. |
| 7,110,803 B2 | 9/2006 | Shults et al. |
| 7,113,821 B1 | 9/2006 | Sun et al. |
| 7,134,999 B2 | 11/2006 | Brauker et al. |
| 7,136,689 B2 | 11/2006 | Shults et al. |
| 7,171,274 B2 | 1/2007 | Starkweather et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,207,974 B2 | 4/2007 | Safabash et al. |
| 7,226,978 B2 | 6/2007 | Tapsak et al. |
| 7,276,029 B2 | 10/2007 | Goode, Jr. et al. |
| 7,278,983 B2 | 10/2007 | Ireland et al. |
| 7,297,151 B2 | 11/2007 | Boecker et al. |
| 7,299,082 B2 | 11/2007 | Feldman et al. |
| 7,310,544 B2 | 12/2007 | Brister et al. |
| 7,318,816 B2 | 1/2008 | Bobroff et al. |
| 7,324,012 B2 | 1/2008 | Mann et al. |
| 7,329,239 B2 | 2/2008 | Safabash et al. |
| 7,335,294 B2 | 2/2008 | Heller et al. |
| 7,340,287 B2 | 3/2008 | Mason et al. |
| 7,340,309 B2 | 3/2008 | Miazga et al. |
| 7,354,420 B2 | 4/2008 | Steil et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,381,184 B2 | 6/2008 | Funderburk et al. |
| 7,402,153 B2 | 7/2008 | Steil et al. |
| 7,407,493 B2 | 8/2008 | Cane |
| 7,416,541 B2 | 8/2008 | Yuzhakov et al. |
| 7,424,318 B2 | 9/2008 | Brister et al. |
| 7,455,663 B2 | 11/2008 | Bikovsky |
| 7,460,898 B2 | 12/2008 | Brister et al. |
| 7,467,003 B2 | 12/2008 | Brister et al. |
| 7,471,972 B2 | 12/2008 | Rhodes et al. |
| 7,494,465 B2 | 2/2009 | Brister et al. |
| 7,497,827 B2 | 3/2009 | Brister et al. |
| 7,519,408 B2 | 4/2009 | Rasdal et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,604,592 B2 | 10/2009 | Freeman et al. |
| 7,613,491 B2 | 11/2009 | Boock et al. |
| 7,615,007 B2 | 11/2009 | Shults et al. |
| 7,632,228 B2 | 12/2009 | Brauker et al. |
| 7,637,868 B2 | 12/2009 | Saint et al. |
| 7,640,048 B2 | 12/2009 | Dobbles et al. |
| 7,651,596 B2 | 1/2010 | Petisce et al. |
| 7,654,956 B2 | 2/2010 | Brister et al. |
| 7,657,297 B2 | 2/2010 | Simpson et al. |
| 7,666,149 B2 | 2/2010 | Simons et al. |
| 7,682,338 B2 | 3/2010 | Griffin |
| 7,697,967 B2 | 4/2010 | Stafford |
| 7,699,807 B2 | 4/2010 | Faust et al. |
| 7,711,402 B2 | 5/2010 | Shults et al. |
| 7,713,574 B2 | 5/2010 | Brister et al. |
| 7,715,893 B2 | 5/2010 | Kamath et al. |
| 7,727,147 B1 | 6/2010 | Osorio et al. |
| 7,731,657 B2 | 6/2010 | Stafford |
| 7,736,344 B2 | 6/2010 | Moberg et al. |
| 7,757,022 B2 | 7/2010 | Kato et al. |
| 7,763,042 B2 | 7/2010 | Iio et al. |
| 7,822,454 B1 | 10/2010 | Alden et al. |
| 7,850,652 B2 | 12/2010 | Liniger et al. |
| 7,896,844 B2 | 3/2011 | Thalmann et al. |
| 7,955,297 B2 | 6/2011 | Radmer et al. |
| 7,985,203 B2 | 7/2011 | Haueter et al. |
| 8,172,805 B2 | 5/2012 | Mogensen et al. |
| 8,262,618 B2 | 9/2012 | Scheurer |
| 8,409,145 B2 | 4/2013 | Raymond et al. |
| 8,641,674 B2 | 2/2014 | Bobroff et al. |
| 8,870,822 B2 | 10/2014 | Thalmann et al. |
| 8,880,138 B2 | 11/2014 | Cho |
| 9,007,781 B2 | 4/2015 | Moein et al. |
| 9,215,992 B2 | 12/2015 | Donnay et al. |
| 9,295,786 B2 | 3/2016 | Gottlieb et al. |
| 2001/0056262 A1 | 12/2001 | Cabin et al. |
| 2002/0013538 A1 | 1/2002 | Teller |
| 2002/0019022 A1 | 2/2002 | Dunn et al. |
| 2002/0019606 A1 | 2/2002 | Lebel et al. |
| 2002/0022855 A1 | 2/2002 | Bobroff et al. |
| 2002/0023852 A1 | 2/2002 | McIvor et al. |
| 2002/0042090 A1 | 4/2002 | Heller et al. |
| 2002/0055711 A1 | 5/2002 | Lavi et al. |
| 2002/0057993 A1 | 5/2002 | Maisey et al. |
| 2002/0066764 A1 | 6/2002 | Perry et al. |
| 2002/0076966 A1 | 6/2002 | Carron et al. |
| 2002/0082487 A1 | 6/2002 | Kollias et al. |
| 2002/0103499 A1 | 8/2002 | Perez et al. |
| 2002/0106709 A1 | 8/2002 | Potts et al. |
| 2002/0119711 A1 | 8/2002 | Van Antwerp et al. |
| 2002/0124017 A1 | 9/2002 | Mault |
| 2002/0128594 A1 | 9/2002 | Das et al. |
| 2002/0130042 A1 | 9/2002 | Moerman et al. |
| 2002/0151796 A1 | 10/2002 | Koulik |
| 2002/0151816 A1 | 10/2002 | Rich et al. |
| 2002/0154050 A1 | 10/2002 | Krupp et al. |
| 2002/0161288 A1 | 10/2002 | Shin et al. |
| 2002/0165462 A1 | 11/2002 | Westbrook et al. |
| 2002/0169369 A1 | 11/2002 | Ward et al. |
| 2002/0198444 A1 | 12/2002 | Ughigaki et al. |
| 2003/0023317 A1 | 1/2003 | Brauker et al. |
| 2003/0023461 A1 | 1/2003 | Quintanilla et al. |
| 2003/0032867 A1 | 2/2003 | Crothall et al. |
| 2003/0042137 A1 | 3/2003 | Mao et al. |

(56) References Cited

U.S. PATENT DOCUMENTS

| | | |
|---|---|---|
| 2003/0060753 A1 | 3/2003 | Starkweather et al. |
| 2003/0065308 A1 | 4/2003 | Lebel et al. |
| 2003/0069510 A1 | 4/2003 | Semler |
| 2003/0078481 A1 | 4/2003 | McIvor et al. |
| 2003/0078560 A1 | 4/2003 | Miller et al. |
| 2003/0083686 A1 | 5/2003 | Freeman et al. |
| 2003/0097092 A1 | 5/2003 | Flaherty |
| 2003/0100040 A1 | 5/2003 | Bonnecaze et al. |
| 2003/0109775 A1 | 6/2003 | O'Neil et al. |
| 2003/0134347 A1 | 7/2003 | Heller et al. |
| 2003/0135333 A1 | 7/2003 | Aceti et al. |
| 2003/0144581 A1 | 7/2003 | Conn et al. |
| 2003/0144608 A1 | 7/2003 | Kojima et al. |
| 2003/0155656 A1 | 8/2003 | Chiu et al. |
| 2003/0168338 A1 | 9/2003 | Gao et al. |
| 2003/0176933 A1 | 9/2003 | Lebel et al. |
| 2003/0187338 A1 | 10/2003 | Say et al. |
| 2003/0199790 A1 | 10/2003 | Boecker et al. |
| 2003/0199910 A1 | 10/2003 | Boecker et al. |
| 2003/0212379 A1 | 11/2003 | Bylund et al. |
| 2003/0217966 A1 | 11/2003 | Tapsak et al. |
| 2003/0225361 A1 | 12/2003 | Sabra |
| 2004/0002382 A1 | 1/2004 | Kovelman et al. |
| 2004/0010207 A1 | 1/2004 | Flaherty et al. |
| 2004/0011671 A1 | 1/2004 | Shults et al. |
| 2004/0040840 A1 | 3/2004 | Mao et al. |
| 2004/0045879 A1 | 3/2004 | Shults et al. |
| 2004/0054263 A1 | 3/2004 | Moerman et al. |
| 2004/0064068 A1 | 4/2004 | DeNuzzio et al. |
| 2004/0064133 A1 | 4/2004 | Miller et al. |
| 2004/0096959 A1 | 5/2004 | Stiene et al. |
| 2004/0106858 A1 | 6/2004 | Say et al. |
| 2004/0106859 A1 | 6/2004 | Say et al. |
| 2004/0116847 A1 | 6/2004 | Wall |
| 2004/0116865 A1 | 6/2004 | Bengtsson |
| 2004/0116866 A1 | 6/2004 | Gorman et al. |
| 2004/0122353 A1 | 6/2004 | Shahmirian et al. |
| 2004/0122489 A1 | 6/2004 | Mazar et al. |
| 2004/0133164 A1 | 7/2004 | Funderbunk et al. |
| 2004/0135684 A1 | 7/2004 | Steinthal et al. |
| 2004/0138544 A1 | 7/2004 | Ward et al. |
| 2004/0138588 A1 | 7/2004 | Saikley et al. |
| 2004/0138688 A1 | 7/2004 | Giraud |
| 2004/0147996 A1 | 7/2004 | Miazga et al. |
| 2004/0152622 A1 | 8/2004 | Keith et al. |
| 2004/0158207 A1 | 8/2004 | Hunn et al. |
| 2004/0167801 A1 | 8/2004 | Say et al. |
| 2004/0171910 A1 | 9/2004 | Moore-Steele |
| 2004/0171921 A1 | 9/2004 | Say et al. |
| 2004/0176672 A1 | 9/2004 | Silver et al. |
| 2004/0186362 A1 | 9/2004 | Brauker et al. |
| 2004/0186365 A1 | 9/2004 | Jin et al. |
| 2004/0193090 A1 | 9/2004 | Lebel et al. |
| 2004/0199059 A1 | 10/2004 | Brauker et al. |
| 2004/0204687 A1 | 10/2004 | Mogensen et al. |
| 2004/0210122 A1 | 10/2004 | Sleburg |
| 2004/0223985 A1 | 11/2004 | Dunfield et al. |
| 2004/0225262 A1 | 11/2004 | Fathallah et al. |
| 2004/0225338 A1 | 11/2004 | Lebel et al. |
| 2004/0236200 A1 | 11/2004 | Say et al. |
| 2004/0236251 A1 | 11/2004 | Roe et al. |
| 2004/0254433 A1 | 12/2004 | Bandis et al. |
| 2004/0254434 A1 | 12/2004 | Goodnow et al. |
| 2004/0267300 A1 | 12/2004 | Mace et al. |
| 2005/0003470 A1 | 1/2005 | Nelson et al. |
| 2005/0004494 A1 | 1/2005 | Perez et al. |
| 2005/0006122 A1 | 1/2005 | Burnette |
| 2005/0010269 A1 | 1/2005 | Lebel et al. |
| 2005/0022599 A1 | 2/2005 | Suzuki |
| 2005/0027177 A1 | 2/2005 | Shin et al. |
| 2005/0027180 A1 | 2/2005 | Goode, Jr. et al. |
| 2005/0031689 A1 | 2/2005 | Shults et al. |
| 2005/0043598 A1 | 2/2005 | Goode, Jr. et al. |
| 2005/0070819 A1 | 3/2005 | Poux et al. |
| 2005/0085872 A1 | 4/2005 | Yanagihara et al. |
| 2005/0090607 A1 | 4/2005 | Tapsak et al. |
| 2005/0090850 A1 | 4/2005 | Thoes et al. |
| 2005/0101912 A1* | 5/2005 | Faust ............... A61M 5/158 604/117 |
| 2005/0106713 A1 | 5/2005 | Phan et al. |
| 2005/0112169 A1 | 5/2005 | Brauker et al. |
| 2005/0114068 A1 | 5/2005 | Chey et al. |
| 2005/0121322 A1 | 6/2005 | Say et al. |
| 2005/0131346 A1 | 6/2005 | Douglas |
| 2005/0143635 A1 | 6/2005 | Kamath et al. |
| 2005/0154410 A1 | 7/2005 | Conway et al. |
| 2005/0165404 A1 | 7/2005 | Miller |
| 2005/0173245 A1 | 8/2005 | Feldman et al. |
| 2005/0176136 A1 | 8/2005 | Burd et al. |
| 2005/0182306 A1 | 8/2005 | Sloan |
| 2005/0187720 A1 | 8/2005 | Goode, Jr. et al. |
| 2005/0192557 A1 | 9/2005 | Brauker et al. |
| 2005/0195930 A1 | 9/2005 | Spital et al. |
| 2005/0197554 A1 | 9/2005 | Polcha |
| 2005/0199494 A1 | 9/2005 | Say et al. |
| 2005/0203360 A1 | 9/2005 | Brauker et al. |
| 2005/0222518 A1 | 10/2005 | Dib |
| 2005/0235156 A1 | 10/2005 | Drucker et al. |
| 2005/0236277 A9 | 10/2005 | Imran et al. |
| 2005/0239154 A1 | 10/2005 | Feldman et al. |
| 2005/0241957 A1 | 11/2005 | Mao et al. |
| 2005/0245795 A1 | 11/2005 | Goode, Jr. et al. |
| 2005/0245799 A1 | 11/2005 | Brauker et al. |
| 2005/0245844 A1 | 11/2005 | Mace et al. |
| 2005/0277164 A1 | 12/2005 | Drucker et al. |
| 2005/0283114 A1 | 12/2005 | Bresina et al. |
| 2005/0287620 A1 | 12/2005 | Heller et al. |
| 2006/0001538 A1 | 1/2006 | Kraft et al. |
| 2006/0004303 A1 | 1/2006 | Weidenhaupt et al. |
| 2006/0009727 A1 | 1/2006 | O'Mahony et al. |
| 2006/0010098 A1 | 1/2006 | Goodnow et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0047220 A1 | 3/2006 | Sakata et al. |
| 2006/0036145 A1 | 4/2006 | Chambers et al. |
| 2006/0081469 A1 | 4/2006 | Lee |
| 2006/0129173 A1 | 6/2006 | Wilkinson |
| 2006/0155210 A1 | 7/2006 | Beckman et al. |
| 2006/0155317 A1 | 7/2006 | List et al. |
| 2006/0166629 A1 | 7/2006 | Reggiardo |
| 2006/0173444 A1 | 8/2006 | Choy et al. |
| 2006/0189863 A1 | 8/2006 | Peyser et al. |
| 2006/0189939 A1 | 8/2006 | Gonnelli et al. |
| 2006/0195029 A1 | 8/2006 | Shults et al. |
| 2006/0200181 A1 | 9/2006 | Fukuzawa et al. |
| 2006/0200970 A1 | 9/2006 | Brister et al. |
| 2006/0222566 A1 | 10/2006 | Brauker et al. |
| 2006/0224171 A1 | 10/2006 | Sakata et al. |
| 2006/0226985 A1 | 10/2006 | Goodnow et al. |
| 2006/0247508 A1 | 11/2006 | Fennell |
| 2006/0253086 A1 | 11/2006 | Moberg et al. |
| 2006/0258929 A1 | 11/2006 | Goode et al. |
| 2006/0264888 A1 | 11/2006 | Moberg et al. |
| 2006/0276724 A1 | 12/2006 | Freeman et al. |
| 2006/0282042 A1 | 12/2006 | Walters et al. |
| 2006/0287591 A1 | 12/2006 | Ocvirk et al. |
| 2007/0016381 A1 | 1/2007 | Kamath et al. |
| 2007/0027381 A1 | 2/2007 | Stafford |
| 2007/0038044 A1 | 2/2007 | Dobbles et al. |

(56) References Cited

U.S. PATENT DOCUMENTS

| | | |
|---|---|---|
| 2007/0060814 A1 | 3/2007 | Stafford |
| 2007/0073129 A1 | 3/2007 | Shah et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0088377 A1 | 4/2007 | Levaughn et al. |
| 2007/0106135 A1 | 5/2007 | Sloan et al. |
| 2007/0110124 A1 | 5/2007 | Zaragoza et al. |
| 2007/0123819 A1 | 5/2007 | Mernoe et al. |
| 2007/0149875 A1 | 6/2007 | Ouyang et al. |
| 2007/0156094 A1 | 7/2007 | Safabash et al. |
| 2007/0163880 A1 | 7/2007 | Woo et al. |
| 2007/0173706 A1 | 7/2007 | Neinast et al. |
| 2007/0173741 A1 | 7/2007 | Deshmukh et al. |
| 2007/0191701 A1 | 8/2007 | Feldman et al. |
| 2007/0203407 A1 | 8/2007 | Hoss et al. |
| 2007/0203966 A1 | 8/2007 | Brauker et al. |
| 2007/0213611 A1 | 9/2007 | Simpson et al. |
| 2007/0235331 A1 | 10/2007 | Simpson et al. |
| 2007/0244368 A1 | 10/2007 | Bayloff et al. |
| 2007/0244398 A1 | 10/2007 | Lo et al. |
| 2007/0249922 A1 | 10/2007 | Peyser et al. |
| 2007/0255302 A1 | 11/2007 | Koeppel et al. |
| 2008/0004512 A1 | 1/2008 | Funderburk et al. |
| 2008/0004573 A1 | 1/2008 | Kaufmann et al. |
| 2008/0009692 A1 | 1/2008 | Stafford |
| 2008/0009805 A1 | 1/2008 | Ethelfeld |
| 2008/0017522 A1 | 1/2008 | Heller et al. |
| 2008/0021666 A1 | 1/2008 | Goode, Jr. et al. |
| 2008/0027474 A1 | 1/2008 | Curry et al. |
| 2008/0029391 A1 | 2/2008 | Mao et al. |
| 2008/0031941 A1 | 2/2008 | Pettersson |
| 2008/0033254 A1 | 2/2008 | Kamath et al. |
| 2008/0033268 A1 | 2/2008 | Stafford |
| 2008/0033318 A1 | 2/2008 | Mace et al. |
| 2008/0039702 A1 | 2/2008 | Hayter et al. |
| 2008/0045824 A1 | 2/2008 | Tapsak et al. |
| 2008/0064937 A1 | 3/2008 | McGarraugh et al. |
| 2008/0064941 A1 | 3/2008 | Funderburk et al. |
| 2008/0064944 A1 | 3/2008 | VanAntwerp et al. |
| 2008/0065646 A1 | 3/2008 | Zhang et al. |
| 2008/0071156 A1 | 3/2008 | Brister et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0097246 A1 | 4/2008 | Stafford |
| 2008/0108942 A1 | 5/2008 | Brister et al. |
| 2008/0112848 A1 | 5/2008 | Huffstodt et al. |
| 2008/0114280 A1 | 5/2008 | Stafford |
| 2008/0119707 A1 | 5/2008 | Stafford |
| 2008/0133702 A1 | 6/2008 | Sharma et al. |
| 2008/0154205 A1 | 6/2008 | Wojcik |
| 2008/0161664 A1 | 7/2008 | Mastrototaro et al. |
| 2008/0167578 A1 | 7/2008 | Bryer et al. |
| 2008/0183061 A1 | 7/2008 | Goode, Jr. et al. |
| 2008/0183399 A1 | 7/2008 | Goode, Jr. et al. |
| 2008/0188731 A1 | 8/2008 | Brister et al. |
| 2008/0189051 A1 | 8/2008 | Goode, Jr. et al. |
| 2008/0194935 A1 | 8/2008 | Brister et al. |
| 2008/0194936 A1 | 8/2008 | Goode, Jr. et al. |
| 2008/0194937 A1 | 8/2008 | Goode, Jr. et al. |
| 2008/0194938 A1 | 8/2008 | Brister et al. |
| 2008/0195049 A1 | 8/2008 | Thalmann et al. |
| 2008/0195232 A1 | 8/2008 | Carr-Brendel et al. |
| 2008/0195967 A1 | 8/2008 | Goode, Jr. et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0200897 A1 | 8/2008 | Hoss et al. |
| 2008/0208025 A1 | 8/2008 | Shults et al. |
| 2008/0214481 A1 | 9/2008 | Challoner et al. |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0242961 A1 | 10/2008 | Brister et al. |
| 2008/0262469 A1 | 10/2008 | Brister et al. |
| 2008/0269673 A1 | 10/2008 | Butoi et al. |
| 2008/0275313 A1 | 11/2008 | Brister et al. |
| 2008/0283396 A1 | 11/2008 | Wang et al. |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0294096 A1 | 11/2008 | Uber et al. |
| 2008/0296155 A1 | 12/2008 | Shults et al. |
| 2008/0300476 A1 | 12/2008 | Stafford |
| 2008/0306368 A1 | 12/2008 | Goode, Jr. et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0312859 A1 | 12/2008 | Skyggebjerg et al. |
| 2009/0005659 A1 | 1/2009 | Kollias et al. |
| 2009/0012377 A1 | 1/2009 | Jennewine et al. |
| 2009/0012379 A1 | 1/2009 | Goode, Jr. et al. |
| 2009/0018424 A1 | 1/2009 | Kamath et al. |
| 2009/0030294 A1 | 1/2009 | Petisce et al. |
| 2009/0036758 A1 | 2/2009 | Brauker et al. |
| 2009/0036763 A1 | 2/2009 | Brauker et al. |
| 2009/0036915 A1 | 2/2009 | Karbowniczek et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0048499 A1 | 2/2009 | Glejbol |
| 2009/0054866 A1 | 2/2009 | Teisen-Simony et al. |
| 2009/0062633 A1 | 3/2009 | Brauker et al. |
| 2009/0062635 A1 | 3/2009 | Brauker et al. |
| 2009/0069658 A1 | 3/2009 | Say et al. |
| 2009/0069750 A1 | 3/2009 | Schraga |
| 2009/0076356 A1 | 3/2009 | Simpson et al. |
| 2009/0076359 A1 | 3/2009 | Peyser |
| 2009/0076360 A1 | 3/2009 | Brister et al. |
| 2009/0076361 A1 | 3/2009 | Kamath et al. |
| 2009/0088614 A1 | 4/2009 | Taub |
| 2009/0088787 A1 | 4/2009 | Koike et al. |
| 2009/0099436 A1 | 4/2009 | Brister et al. |
| 2009/0102678 A1 | 4/2009 | Mazza et al. |
| 2009/0105569 A1 | 4/2009 | Stafford |
| 2009/0124877 A1 | 5/2009 | Goode, Jr. et al. |
| 2009/0124878 A1 | 5/2009 | Goode, Jr. et al. |
| 2009/0124879 A1 | 5/2009 | Brister et al. |
| 2009/0124964 A1 | 5/2009 | Leach et al. |
| 2009/0124979 A1 | 5/2009 | Raymond et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0131860 A1 | 5/2009 | Nielson |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0171182 A1 | 7/2009 | Stafford |
| 2009/0178459 A1 | 7/2009 | Li et al. |
| 2009/0182217 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0198215 A1 | 8/2009 | Chong et al. |
| 2009/0203981 A1 | 8/2009 | Brauker et al. |
| 2009/0204341 A1 | 8/2009 | Brauker et al. |
| 2009/0212766 A1 | 8/2009 | Olson et al. |
| 2009/0216103 A1 | 8/2009 | Brister et al. |

(56) References Cited

U.S. PATENT DOCUMENTS

| | | |
|---|---|---|
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0259118 A1 | 10/2009 | Feldman et al. |
| 2009/0259201 A1 | 10/2009 | Hwang et al. |
| 2009/0259202 A1 | 10/2009 | Leeflang et al. |
| 2009/0270765 A1 | 10/2009 | Ghesquire et al. |
| 2009/0287073 A1 | 11/2009 | Boock et al. |
| 2009/0287074 A1 | 11/2009 | Shults et al. |
| 2009/0292184 A1 | 11/2009 | Funderburk et al. |
| 2009/0292185 A1 | 11/2009 | Funderburk et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299167 A1 | 12/2009 | Seymour |
| 2009/0299276 A1 | 12/2009 | Brauker et al. |
| 2009/0299301 A1* | 12/2009 | Gottlieb ............ A61M 37/0069 604/263 |
| 2010/0004597 A1 | 1/2010 | Gryn et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0022863 A1 | 1/2010 | Mogensen et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0036281 A1 | 2/2010 | Doi |
| 2010/0041971 A1 | 2/2010 | Goode, Jr. et al. |
| 2010/0045465 A1 | 2/2010 | Brauker et al. |
| 2010/0049014 A1 | 2/2010 | Funderburk et al. |
| 2010/0049024 A1 | 2/2010 | Saint et al. |
| 2010/0063373 A1 | 3/2010 | Kamath et al. |
| 2010/0076283 A1 | 3/2010 | Simpson et al. |
| 2010/0081908 A1 | 4/2010 | Dobbles et al. |
| 2010/0081910 A1 | 4/2010 | Brister et al. |
| 2010/0087724 A1 | 4/2010 | Brauker et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0106088 A1 | 4/2010 | Yodfat et al. |
| 2010/0113894 A1 | 5/2010 | Brenneman et al. |
| 2010/0119693 A1 | 5/2010 | Tapsak et al. |
| 2010/0121169 A1 | 5/2010 | Petisce et al. |
| 2010/0152674 A1 | 6/2010 | Kavazov et al. |
| 2010/0168677 A1 | 7/2010 | Gabriel et al. |
| 2010/0174157 A1 | 7/2010 | Brister et al. |
| 2010/0174158 A1 | 7/2010 | Kamath et al. |
| 2010/0174163 A1 | 7/2010 | Brister et al. |
| 2010/0174164 A1 | 7/2010 | Brister et al. |
| 2010/0174165 A1 | 7/2010 | Brister et al. |
| 2010/0174166 A1 | 7/2010 | Brister et al. |
| 2010/0174167 A1 | 7/2010 | Kamath et al. |
| 2010/0174168 A1 | 7/2010 | Goode, Jr. et al. |
| 2010/0179401 A1 | 7/2010 | Rasdal et al. |
| 2010/0179402 A1 | 7/2010 | Goode, Jr. et al. |
| 2010/0179404 A1 | 7/2010 | Kamath et al. |
| 2010/0179408 A1 | 7/2010 | Kamath et al. |
| 2010/0179409 A1 | 7/2010 | Kamath et al. |
| 2010/0185065 A1 | 7/2010 | Goode, Jr. et al. |
| 2010/0186069 A1 | 7/2010 | Brister et al. |
| 2010/0186070 A1 | 7/2010 | Brister et al. |
| 2010/0186071 A1 | 7/2010 | Simpson et al. |
| 2010/0186072 A1 | 7/2010 | Goode, Jr. et al. |
| 2010/0186075 A1 | 7/2010 | Brister et al. |
| 2010/0191082 A1 | 7/2010 | Brister et al. |
| 2010/0198033 A1 | 8/2010 | Krulevitch et al. |
| 2010/0198034 A1 | 8/2010 | Thomas et al. |
| 2010/0198035 A1 | 8/2010 | Kamath et al. |
| 2010/0198036 A1 | 8/2010 | Kamath et al. |
| 2010/0204653 A1 | 8/2010 | Gryn et al. |
| 2010/0212583 A1 | 8/2010 | Brister et al. |
| 2010/0214104 A1 | 8/2010 | Goode, Jr. et al. |
| 2010/0217105 A1 | 8/2010 | Yodfat et al. |
| 2010/0217557 A1 | 8/2010 | Kamath et al. |
| 2010/0223013 A1 | 9/2010 | Kamath et al. |
| 2010/0223022 A1 | 9/2010 | Kamath et al. |
| 2010/0223023 A1 | 9/2010 | Kamath et al. |
| 2010/0228109 A1 | 9/2010 | Kamath et al. |
| 2010/0228497 A1 | 9/2010 | Kamath et al. |
| 2010/0240975 A1 | 9/2010 | Goode, Jr. et al. |
| 2010/0240976 A1 | 9/2010 | Goode, Jr. et al. |
| 2010/0151987 A1 | 10/2010 | Kamath et al. |
| 2010/0256471 A1 | 10/2010 | Say et al. |
| 2010/0262201 A1 | 10/2010 | He et al. |
| 2010/0274107 A1 | 10/2010 | Boock et al. |
| 2010/0280341 A1 | 11/2010 | Boock et al. |
| 2010/0286496 A1 | 11/2010 | Simpson et al. |
| 2010/0298684 A1 | 11/2010 | Leach et al. |
| 2010/0324392 A1 | 12/2010 | Yee et al. |
| 2010/0324403 A1 | 12/2010 | Brister et al. |
| 2010/0331642 A1 | 12/2010 | Bruce et al. |
| 2010/0331644 A1 | 12/2010 | Neale et al. |
| 2010/0331647 A1 | 12/2010 | Shah et al. |
| 2010/0331648 A1 | 12/2010 | Kamath et al. |
| 2010/0331653 A1 | 12/2010 | Stafford |
| 2010/0331656 A1 | 12/2010 | Mensinger et al. |
| 2010/0331657 A1 | 12/2010 | Mensinger et al. |
| 2011/0004085 A1 | 1/2011 | Mensinger et al. |
| 2011/0009727 A1 | 1/2011 | Mensinger et al. |
| 2011/0021889 A1 | 1/2011 | Hoss et al. |
| 2011/0024043 A1 | 2/2011 | Boock et al. |
| 2011/0024307 A1 | 2/2011 | Simpson et al. |
| 2011/0027127 A1 | 2/2011 | Simpson et al. |
| 2011/0027453 A1 | 2/2011 | Boock et al. |
| 2011/0027458 A1 | 2/2011 | Boock et al. |
| 2011/0028815 A1 | 2/2011 | Simpson et al. |
| 2011/0028816 A1 | 2/2011 | Simpson et al. |
| 2011/0046456 A1 | 2/2011 | Hordum et al. |
| 2011/0046467 A1 | 2/2011 | Simpson et al. |
| 2011/0240256 A1 | 2/2011 | Bobroff et al. |
| 2011/0240263 A1 | 2/2011 | Hordum et al. |
| 2011/0054275 A1 | 3/2011 | Stafford |
| 2011/0060196 A1 | 3/2011 | Stafford |
| 2011/0073475 A1 | 3/2011 | Kastanos et al. |
| 2011/0077490 A1 | 3/2011 | Simpson et al. |
| 2011/0082484 A1 | 4/2011 | Saravia et al. |
| 2011/0106126 A1 | 5/2011 | Love et al. |
| 2011/0118579 A1 | 5/2011 | Goode, Jr. et al. |
| 2011/0118580 A1 | 5/2011 | Goode, Jr. et al. |
| 2011/0124992 A1 | 5/2011 | Brauker et al. |
| 2011/0124997 A1 | 5/2011 | Goode, Jr. et al. |
| 2011/0125410 A1 | 5/2011 | Goode, Jr. et al. |
| 2011/0130970 A1 | 6/2011 | Goode, Jr. et al. |
| 2011/0130971 A1 | 6/2011 | Goode, Jr. et al. |
| 2011/0130998 A1 | 6/2011 | Goode, Jr. et al. |
| 2011/0137257 A1 | 6/2011 | Gyrn et al. |
| 2011/0144465 A1 | 6/2011 | Shults et al. |
| 2011/0172510 A1 | 7/2011 | Chickering, III et al. |
| 2011/0178378 A1 | 7/2011 | Brister et al. |
| 2011/0178461 A1 | 7/2011 | Chong et al. |
| 2011/0184258 A1 | 7/2011 | Stafford |
| 2011/0190603 A1 | 8/2011 | Stafford |
| 2011/0190614 A1 | 8/2011 | Brister et al. |
| 2011/0191044 A1 | 8/2011 | Stafford |
| 2011/0201910 A1 | 8/2011 | Rasdal et al. |
| 2011/0201911 A1 | 8/2011 | Johnson et al. |
| 2011/0213225 A1 | 9/2011 | Bernstein et al. |
| 2011/0218414 A1 | 9/2011 | Kamath et al. |
| 2011/0231107 A1 | 9/2011 | Brauker et al. |
| 2011/0231140 A1 | 9/2011 | Goode, Jr. et al. |
| 2011/0231141 A1 | 9/2011 | Goode, Jr. et al. |

(56) References Cited

U.S. PATENT DOCUMENTS

| | | | |
|---|---|---|---|
| 2011/0231142 A1 | 9/2011 | Goode, Jr. et al. | |
| 2011/0253533 A1 | 10/2011 | Shults et al. | |
| 2011/0257521 A1 | 10/2011 | Fraden | |
| 2011/0257895 A1 | 10/2011 | Brauker et al. | |
| 2011/0263958 A1 | 10/2011 | Brauker et al. | |
| 2011/0270062 A1 | 11/2011 | Goode, Jr. et al. | |
| 2011/0270158 A1 | 11/2011 | Brauker et al. | |
| 2011/0275919 A1 | 11/2011 | Petisce et al. | |
| 2011/0288574 A1 | 11/2011 | Donnay et al. | |
| 2011/0290645 A1 | 12/2011 | Brister et al. | |
| 2011/0313543 A1 | 12/2011 | Brauker et al. | |
| 2011/0319729 A1 | 12/2011 | Curry et al. | |
| 2011/0319733 A1 | 12/2011 | Stafford | |
| 2011/0319738 A1 | 12/2011 | Woodruff et al. | |
| 2011/0319739 A1 | 12/2011 | Kamath et al. | |
| 2011/0320130 A1 | 12/2011 | Valdes et al. | |
| 2012/0010642 A1* | 1/2012 | Lee .................. | A61B 5/15194 606/182 |
| 2012/0035445 A1 | 2/2012 | Boock et al. | |
| 2012/0040101 A1 | 2/2012 | Tapsak et al. | |
| 2012/0046534 A1 | 2/2012 | Simpson et al. | |
| 2012/0078071 A1 | 3/2012 | Bohm et al. | |
| 2012/0095406 A1 | 4/2012 | Gyrn et al. | |
| 2012/0108934 A1 | 5/2012 | Valdes et al. | |
| 2012/0108983 A1 | 5/2012 | Banet et al. | |
| 2012/0123385 A1 | 5/2012 | Edwards et al. | |
| 2012/0143135 A1 | 6/2012 | Cole et al. | |
| 2012/0184909 A1 | 7/2012 | Gyrn et al. | |
| 2012/0296327 A1 | 11/2012 | Hutchins et al. | |
| 2013/0047981 A1 | 2/2013 | Bacon | |
| 2013/0150691 A1 | 6/2013 | Pace et al. | |
| 2013/0317323 A1 | 11/2013 | Fujiwara et al. | |
| 2014/0228760 A1 | 8/2014 | Ethelfeld | |
| 2015/0025338 A1 | 1/2015 | Lee et al. | |
| 2015/0073238 A1 | 3/2015 | Matsumoto et al. | |
| 2015/0164545 A1 | 6/2015 | Gyrn | |

FOREIGN PATENT DOCUMENTS

| | | |
|---|---|---|
| EP | 0390390 | 10/1990 |
| EP | 0396788 | 11/1990 |
| EP | 2060284 | 5/2009 |
| EP | 2201969 | 6/2010 |
| EP | 2335587 | 6/2011 |
| WO | WO-1992/013271 | 8/1992 |
| WO | WO-1994/020602 | 9/1994 |
| WO | WO-2000/059370 | 10/2000 |
| WO | WO-2001/052935 | 7/2001 |
| WO | WO-2001/054753 | 8/2001 |
| WO | WO-2003/082091 | 10/2003 |
| WO | WO-2009/068661 | 6/2009 |

OTHER PUBLICATIONS

Alcock, S. J., et al., "Continuous Analyte Monitoring to Aid Clinical Practice", IEEE Engineering in Medicine and Biology Magazine, 1994, pp. 319-325.

Armour, J. C., et al., "Application of Chronic Intravascular Blood Glucose Sensor in Dogs", Diabetes, vol. 39, 1990, pp. 1519-1526.

Aussedat, B., et al., "A User-Friendly Method for Calibrating a Subcutaneous Glucose Sensor-Based Hypoglycaemic Alarm", Biosensors & Bioelectronics, vol. 12, No. 11, 1997, pp. 1061-1071.

Bennion, N., et al., "Alternate Site Glucose Testing: A Crossover Design", Diabetes Technology & Therapeutics, vol. 4, No. 1, 2002, pp. 25-33.

Bindra, D. S., et al., "Design and in Vitro Studies of a Needle-Type Glucose Sensor for Subcutaneous Monitoring", Analytical Chemistry, vol. 63, No. 17, 1991, pp. 1692-1696.

Bindra, D. S., et al., "Pulsed Amperometric Detection of Glucose in Biological Fluids at a Surface-Modified Gold Electrode", Analytical Chemistry, vol. 61, No. 22, 1989, pp. 2566-2570.

Bobbioni-Harsch, E., et al., "Lifespan of Subcutaneous Glucose Sensors and Their Performances During Dynamic Glycaemia Changes in Rats", Journal of Biomedical Engineering, vol. 15, 1993, pp. 457-463.

Cass, A. E., et al., "Ferrocene-Mediated Enzyme Electrode for Amperometric Determination of Glucose", Analytical Chemistry, vol. 56, No. 4, 1984, pp. 667-671.

Claremont, D. J., et al., "Biosensors for Continuous In Vivo Glucose Monitoring", Proceedings of the Annual International Conference of the IEEE Engineering in Medicine and Biology Society, vol. 10, 1988.

Clark Jr., L. C., et al., "Electrode Systems for Continuous Monitoring in Cardiovascular Surgery", Annals New York Academy of Sciences, 1962, pp. 29-43.

Clark Jr., L. C., et al., "Long-term Stability of Electroenzymatic Glucose Sensors Implanted in Mice", American Society of Artificial Internal Organs Transactions, vol. XXXIV, 1988, pp. 259-265.

Csöregi, E., et al., "Design and Optimization of a Selective Subcutaneously Implantable Glucose Electrode Based on 'Wired' Glucose Oxidase", Analytical Chemistry, vol. 67, No. 7, 1995, pp. 1240-1244.

Csöregi, E., et al., "Design, Characterization, and One-Point in Vivo Calibration of a Subcutaneously Implanted Glucose Electrode", Analytical Chemistry, vol. 66, No. 19, 1994, pp. 3131-3138.

Feldman, B., et al., "A Continuous Glucose Sensor Based on Wired Enzyme™ Technology—Results from a 3-Day Trial in Patients with Type 1 Diabetes", Diabetes Technology & Therapeutics, vol. 5, No. 5, 2003, pp. 769-779.

Feldman, B., et al., "Correlation of Glucose Concentrations in Interstitial Fluid and Venous Blood During Periods of Rapid Glucose Change", Abbott Diabetes Care Inc. Freestyle Navigator Continuous Glucose Monitor Pamphlet, 2004.

Gregg, B. A., et al., "Cross-Linked Redox Gels Containing Glucose Oxidase for Amperometric Biosensor Applications", Analytical Chemistry, vol. 62, No. 3, 1990, pp. 258-263.

Gunasingham, et al., "Electrochemically Modulated Optrode for Glucose", Biosensors & Bioelectronics, vol. 7, 1992, pp. 353-359.

Harrison, D. J., et al., "Characterization of Perfluorosulfonic Acid Polymer Coated Enzyme Electrodes and a Miniaturized Integrated Potentiostat for Glucose Analysis in Whole Blood", Analytical Chemistry, vol. 60, No. 19, 1988, pp. 2002-2007.

Heller, A., "Electrical Connection Enzyme Redox Centers to Electrodes", Journal of Physical Chemistry, vol. 96, No. 9, 1990, pp. 3579-3587.

Heller, A., "Electrical Wiring of Redox Enzymes", Accounts of Chemical Research, 1990, vol. 23, No. 5, pp. 128-134.

Ikeda, T., et al., "Artificial Pancreas—Investigation of the Stability of Glucose Sensors Using a Telemetry System" (English translation of abstract), Jpn. J. Artif. Organs, vol. 19, No. 2, 1990, pp. 889-892.

Isermann, R., "Supervision, Fault-Detection and Fault-Diagnosis Methods—An Introduction", Control Engineering Practice, vol. 5, No. 5, 1997, pp. 639-652.

Isermann, R., et al., "Trends in the Application of Model-Based Fault Detection and Diagnosis of Technical Processes", Control Engineering Practice, vol. 5, No. 5, 1997, pp. 709-719.

Johnson, K. W., "Peripheral Circulation", John Wiley & Sons, 1978, pp. 1989.

Johnson, K. W., et al., "In vivo evaluation of an electroenzymatic glucose sensor implanted in subcutaneous tissue", Biosensors & Bioelectronics, vol. 7, 1992, pp. 709-714.

Jungheim, K., et al., "How Rapid Does Glucose Concentration Change in Daily Life of Patients with Type 1 Diabetes?", Diabetologia, 2002, pp. 250.

Jungheim, K., et al., "Risky Delay of Hypoglycemia Detection by Glucose Monitoring at the Arm", Diabetes Care, vol. 24, No. 7, 2001, pp. 1303-1304.

Koudelka, M., et al., "In-Vivo Behaviour of Hypodermically Implanted Microfabricated Glucose Sensors", Biosensors & Bioelectronics, vol. 6, 1991, pp. 31-36.

Lager, W., et al., "Implantable Electrocatalytic Glucose Sensor", Hormone Metabolic Research, vol. 26, 1994, pp. 526-530.

(56) References Cited

OTHER PUBLICATIONS

Maidan, R., et al "Elimination of Electrooxidizable Interferant-Produced Currents in Amperometric Biosensors", Analytical Chemistry, vol. 64, No. 23, 1992, pp. 2889-2896.
Mastrototaro, J. J., et al., "An Electroenzymatic Glucose Sensor Fabricated on a Flexible Substrate", Sensors and Actuators B, vol. 5, 1991, pp. 139-144.
Mckean, B. D., et al., "A Telemetry-Instrumentation System for Chronically Implanted Glucose and Oxygen Sensors", IEEE Transactions on Biomedical Engineering, vol. 35, No. 7, 1988, pp. 526-532.
Minimed Technologies, "Tape Tips and Other Infusion Site Information", 1995, pp. 1-10.
Moatti-Sirat, D., et al., "Evaluating In Vitro and In Vivo the Interference of Ascorbate and Acetaminophen on Glucose Detection by a Needle-Type Glucose Sensor", Biosensors & Bioelectronics, vol. 7, 1992, pp. 345-352.
Moatti-Sirat, D., et al., "Reduction of acetaminophen interference in glucose sensors by a composite Nafion membrane: demonstration in rats and man", Diabetologia, vol. 37, 1994, pp. 610-616.
Moatti-Sirat, D., et al., "Towards continuous glucose monitoring: in vivo evaluation of a miniaturized glucose sensoriImplanted for several days in rat subcutaneous tissue", Diabetologia, vol. 35, 1992, pp. 224-230.
Ohara, T. J., et al., "Glucose Electrodes Based on Cross-Linked [Os(bpy)$_2$Cl]$^{+/2+}$ Complexed Poly(1-vinylimidazole) Films", Analytical Chemistry, vol. 65, No. 23, 1993, pp. 3512-3517.
Olievier, C. N., et al., "In vivo Measurement of Carbon Dioxide Tension with a Miniature Electrode", Pflügers Archiv: European Journal of Physiology, vol. 373, 1978, pp. 269-272.
Pickup, J., et al., "Implantable Glucose Sensors: Choosing the Appropriate Sensing Strategy", Biosensors, vol. 3, 1987/88, pp. 335-346.
Pickup, J., "Developing glucose sensors for in vivo use", Tibtech, vol. 11, 1993, pp. 285-291.
Pickup, J., et al., "Potentially-Implantable, Amperometric Glucose Sensors with Mediated Electron Transfer: Improving the Operating Stability", Biosensors, vol. 4, 1989, pp. 109-119.
Pickup, J., et al., "In vivo molecular sensing in diabetes mellitus: an implantable glucose sensor with direct electron transfer", Diabetologia, vol. 32, 1989, pp. 213-217.
Pishko, M. V., et al., "Amperometric Glucose Microelectrodes Prepared through Immobilization of Glucose Oxidase in Redox Hydrogels", Analytical Chemistry, vol. 63, No. 20, 1991, pp. 2268-2272.
Poitout, V., et al., "A glucose monitoring system for on line estimation in man of blood glucose concentration using a miniaturized glucose sensor implanted in the subcutaneous tissue and a wearable control unit", Diabetolgia, vol. 36, 1993, pp. 658-663.
Poitout, V., et al., "Calibration in dogs of a subcutaneous miniaturized glucose sensor using a glucose meter for blood glucose determination", Biosensors & Bioelectronics, vol. 7, 1992, pp. 587-592.
Poitout, V., et al., "In Vitro and In Vivo Evaluation in Dogs of a Miniaturized Glucose Sensor", ASAIO Transactions, vol. 37, No. 3, 1991, pp. M298-M300.
Quinn, C. P., et al., "Kinetics of glucose delivery to subcutaneous tissue in rats measured with 0.3-mm amperometric microsensors", The American Physiological Society, 1995, pp. E155-E161.
Ratner, B. D., "Reducing capsular thickness and enhancing angiogenesis around implant drug release systems", Journal of Controlled Release, vol. 78, 2002, pp. 211-218.
Reach, G., et al., "Can Continuous Glucose Monitoring Be Used for the Treatment of Diabetes?", Analytical Chemistry, vol. 64, No. 6, 1992, pp. 381-386.
Rebrin, K., et al., "Automated feedback control of subcutaneous glucose concentration in diabetic dogs", Diabetologia, vol. 32, 1989, pp. 573-576.
Roe, J. N., et al., "Bloodless Glucose Measurements", Critical Review in Therapeutic Drug Carrier Systems, vol. 15, No. 3, 1998, pp. 199-241.
Sakakida, M., et al., "Development of ferrocene-mediated needle-type glucose sensor as a measure of true subcutaneous tissue glucose concentrations," Artificial Organs Today, vol. 2, No. 2, 1992, pp. 145-158.
Sakakida, M., et al., "Ferrocene-mediated needle-type glucose sensor covered with newly designed biocompatible membrane", Sensors and Actuators B, vol. 13-14, 1993, pp. 319-322.
Salehi, C., et al., "A Telemetry-Instrumentation System for Long-Term Implantable Glucose and Oxygen Sensors", Analytical Letters, vol. 29, No. 13, 1996, pp. 2289-2308.
Scheller, F., et al., "Enzyme electrodes and their application", Philosophical Transactions of the Royal Society of London B, vol. 316, 1987, pp. 85-94.
Schmidt, F. J., et al., "Calibration of a wearable glucose sensor", The International Journal of Artificial Organs, vol. 15, No. 1, 1992, pp. 55-61.
Schmidtke, D. W., et al., "Measurement and Modeling of the Transient Difference Between Blood and Subcutaneous Glucose Concentrations in the Rat After Injection of Insulin", Proceedings of the National Academy of Sciences, vol. 95, 1998, pp. 294-299.
Shaw, G. W., et al., "In vitro testing of a simply constructed, highly stable glucose sensor suitable for implantation in diabetic patients", Biosensors & Bioelectronics, vol. 6, 1991, pp. 401-406.
Shichiri, M., et al., "Glycaemic Control in Pancreatectomized Dogs with a Wearable Artificial Endocrine Pancreas", Diabetologia, vol. 24, 1983, pp. 179-184.
Shichiri, M., et al., "In Vivo Characteristics of Needle-Type Glucose Sensor—Measurements of Subcutaneous Glucose Concentrations in Human Volunteers", Hormone and Metabolic Research Supplement Series, vol. 20, 1988, pp. 17-20.
Shichiri, M., et al., "Membrane design for extending the long-life of an implantableglucose sensor", Diabetes Nutrition and Metabolism, vol. 2, 1989, pp. 309-313.
Shichiri, M., et al., "Needle-type Glucose Sensor for Wearable Artificial Endocrine Pancreas", Implantable Sensors for Closed-Loop Prosthetic Systems, Chapter 15, 1985, pp. 197-210.
Shichiri, M., et al., "Telemetry Glucose Monitoring Device With Needle-Type Glucose Sensor: A Useful Tool for Blood Glucose Monitoring in Diabetic Individuals", Diabetes Care, vol. 9, No. 3, 1986, pp. 298-301.
Shichiri, M., et al., "Wearable Artificial Endocrine Pancreas With Needle-Type Glucose Sensor", The Lancet, 1982, pp. 1129-1131.
Shults, M. C., et al., "A Telemetry-Instrumentation System for Monitoring Multiple Subcutaneously Implanted Glucose Sensors", IEEE Transactions on Biomedical Engineering, vol. 41, No. 10, 1994, pp. 937-942.
Sternberg, R., et al., "Study and Development of Multilayer Needle-type Enzyme-based Glucose Microsensors", Biosensors, vol. 4, 1988, pp. 27-40.
Thompson, M., et al., "In Vivo Probes: Problems and Perspectives", Clinical Biochemistry, vol. 19, 1986, pp. 255-261.
Turner, A.P.F., et al., "Diabetes Mellitus: Biosensors for Research and Management", Biosensors, vol. 1, 1985, pp. 85-115.
Updike, S. J., et al., "Principles of Long-term Fully Implanted Sensors with Emphasis on Radiotelemetric Monitoring of Blood Glucose from inside a Subcutaneous Foreign Body Capsule (FBC)", Biosensors in the Body: Continuous in vivo Monitoring, Chapter 4, 1997, pp. 117-137.
Updike, S. J., et al., "A Subcutaneous Glucose Sensor With Improved Longevity, Dynamic Range, and Stability of Calibration", Diabetes Care, 2000, vol. 23, pp. 208-214.
Velho, G., et al., "Strategies for calibrating a subcutaneous glucose sensor", Biomedica Biochimica Acta, vol. 48, 1989, pp. 957-964.
Velho, G., et al., "In Vitro and in Vivo Stability of Electrode Potentials in Needle-Type Glucose Sensors", Diabetes, vol. 38, No. 2, 1989, pp. 164-171.
Von Woedtke, T., et al., "In situ calibration of implanted electrochemical glucose sensors", Biomedica Biochimica Acta, vol. 48, 1989, pp. 943-952.

(56) References Cited

OTHER PUBLICATIONS

Wilson, G. S., et al., "Progress toward the Development of an Implantable Sensor for Glucose", Clinical Chemistry, vol. 38, No. 9, 1992, pp. 1613-1617.
Ye, L., et al., "High Current Density 'Wired' Quinoprotein Glucose Dehydrogenase Electrode", Analytical Chemistry, vol. 65, No. 3, 1993, pp. 238-241.
PCT/US2012/068839 ISR and Written Opinion dated Feb. 22, 2013.
NL 2009963 Search Report and Written Opinion dated Aug. 12, 2013.
AU 2011269796 Examination Report dated Apr. 3, 2014.
EP 11760268.0 Extended Search Report dated Apr. 14, 2014.
EP 10739015.5 Extended Search Report dated May 10, 2013.
WO, PCT/US2016/032485 ISR and Written Opinion, dated Sep. 12, 2016.

\* cited by examiner

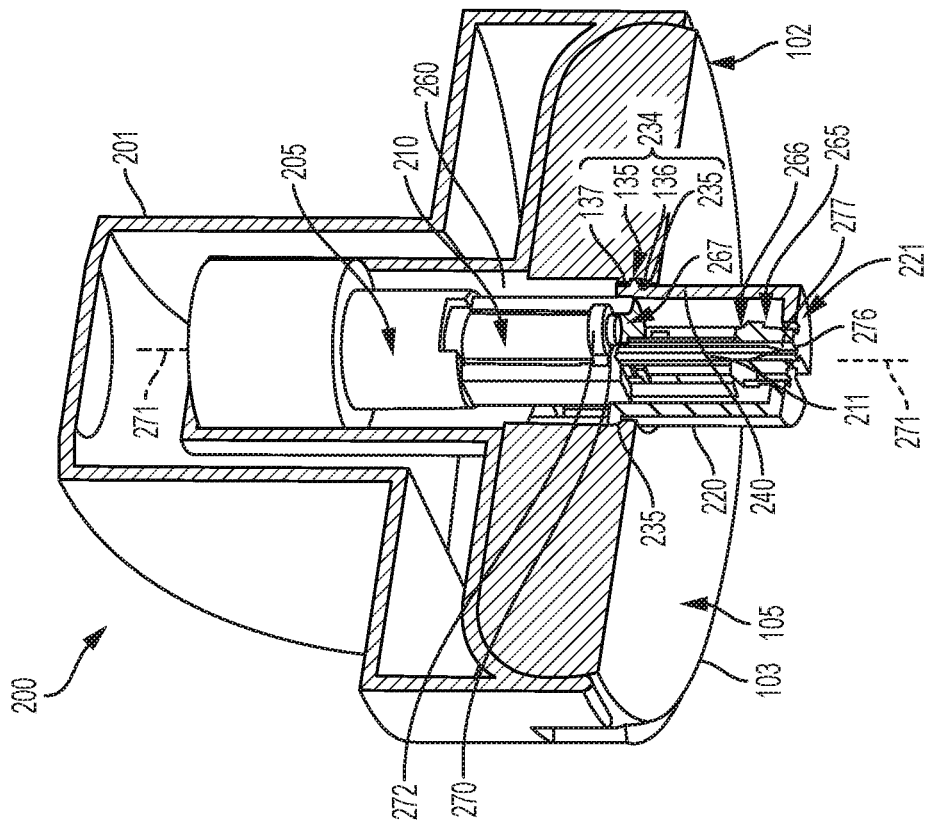
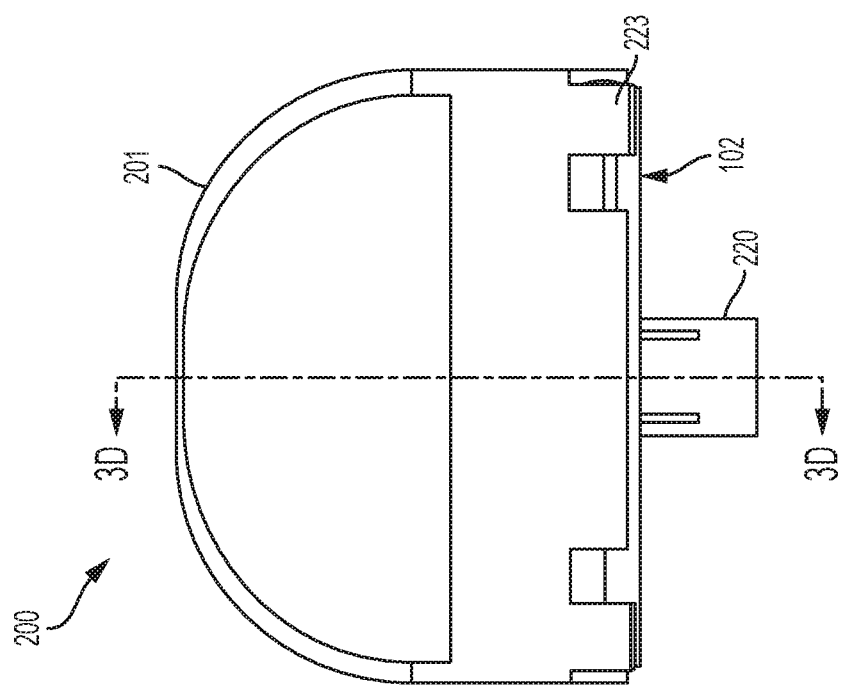
FIG. 3D
FIG. 3C

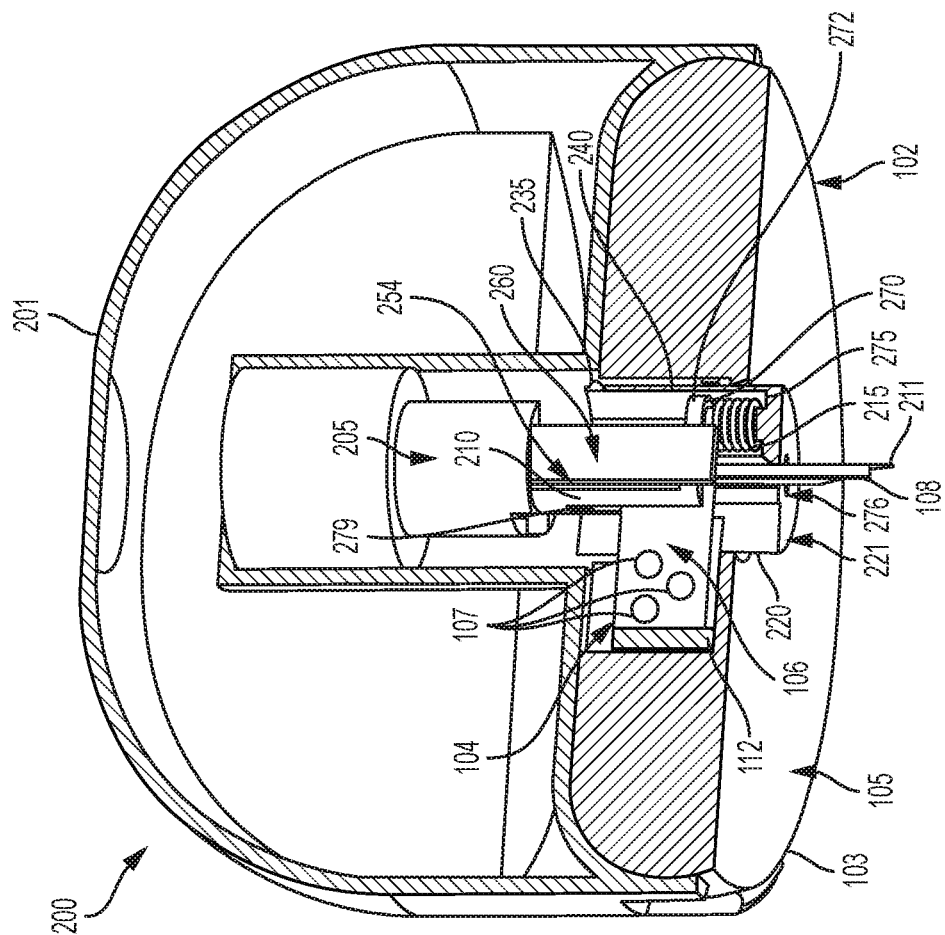
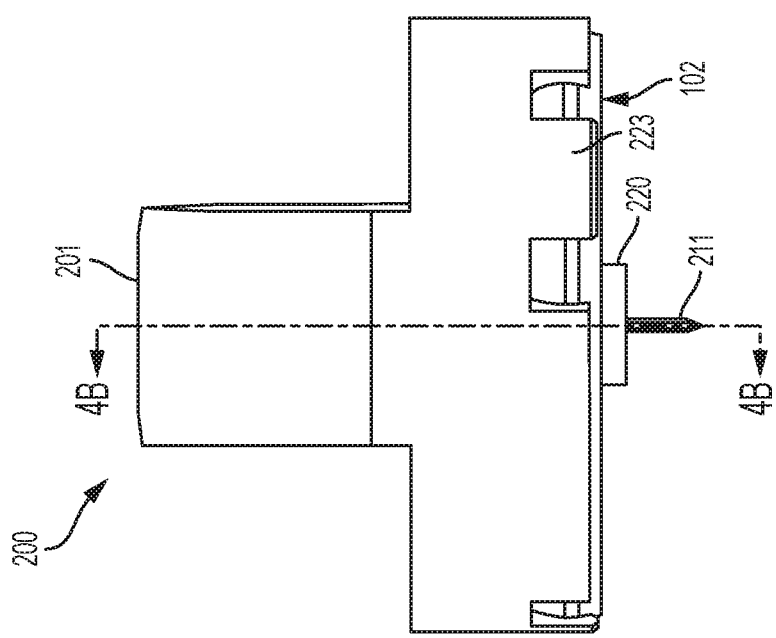
FIG. 4B
FIG. 4A

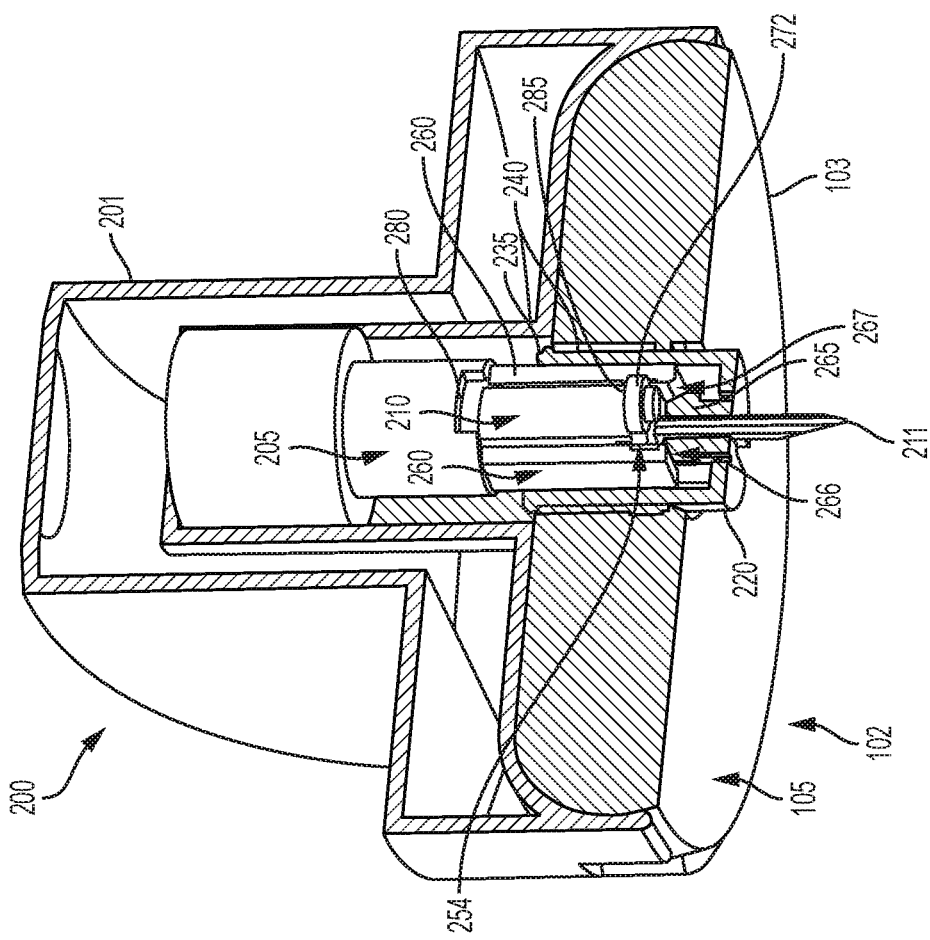
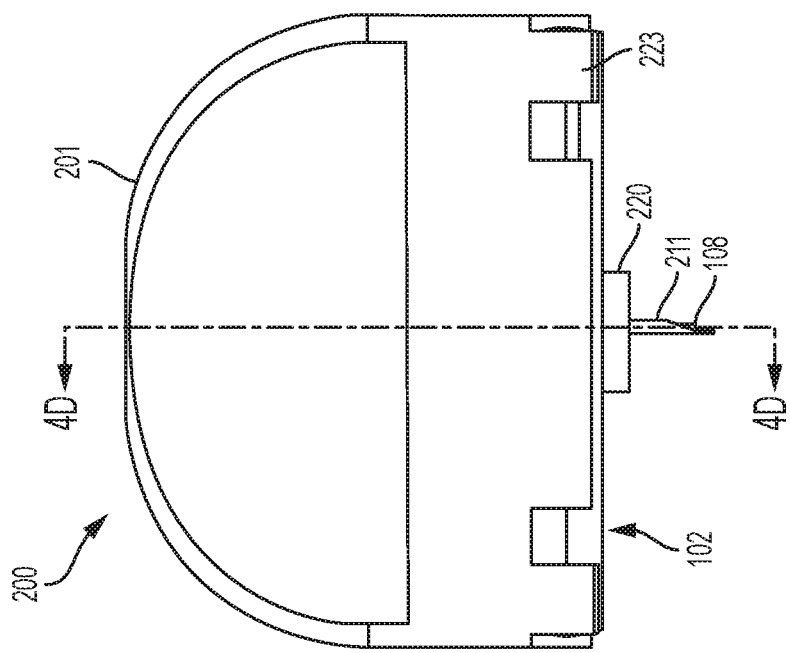
FIG. 4D
FIG. 4C

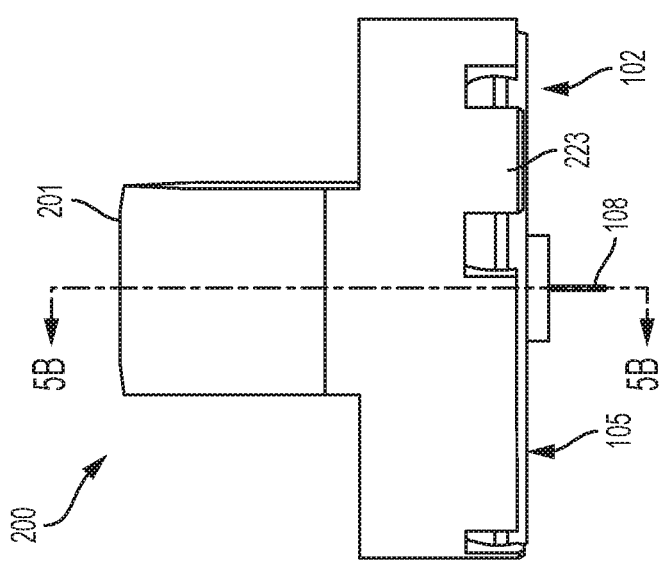
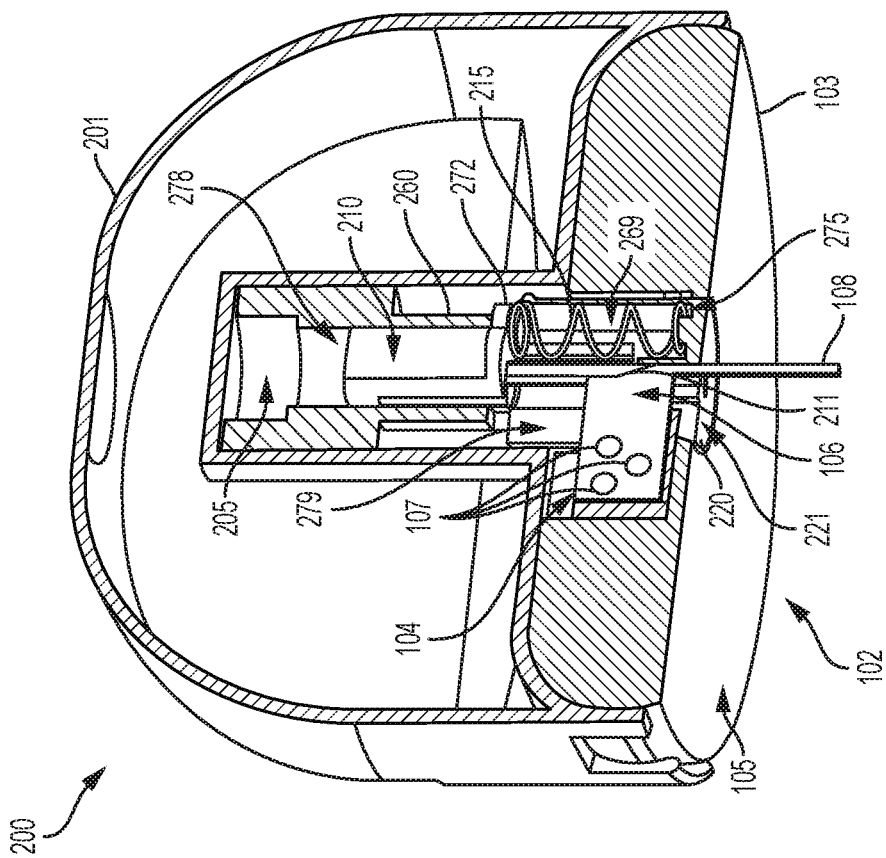
FIG. 5A
FIG. 5B

COMPACT MEDICAL DEVICE INSERTERS AND RELATED SYSTEMS AND METHODS

CROSS-REFERENCE TO RELATED APPLICATIONS

This application claims priority to, and the benefit of, U.S. Provisional Patent Application 62/161,787 filed May 14, 2015, the contents of which are incorporated by reference herein in its entirety and for all purposes.

FIELD

The present subject matter relates to compact medical device inserters for inserting a medical device through the skin of a subject, as well as to systems incorporating or utilizing such inserters and methods for making and using the inserters and incorporating systems.

BACKGROUND

The detection and/or monitoring of glucose levels or other analytes, such as lactate, oxygen, A1C, or the like, in certain individuals is vitally important to their health. For example, the monitoring of glucose is particularly important to individuals with diabetes. Diabetics generally monitor glucose levels to determine if their glucose levels are being maintained within a clinically safe range, and may also use this information to determine if, and/or when, insulin is needed to reduce glucose levels in their bodies or when additional glucose is needed to raise the level of glucose in their bodies.

Growing clinical data demonstrates a strong correlation between the frequency of glucose monitoring and glycemic control. Despite such correlation, many individuals diagnosed with a diabetic condition do not monitor their glucose levels as frequently as they should due to a combination of factors including convenience, testing discretion, pain associated with glucose testing, and cost.

Devices have been developed for the automatic monitoring of analyte(s), such as glucose, in bodily fluid such as in the blood stream or in interstitial fluid ("ISF"), or other biological fluid. Some of these analyte monitoring devices are configured so that at least a portion of the devices are positioned below a skin surface of a user, e.g., in a blood vessel or in the subcutaneous tissue of a user, so that the monitoring is accomplished in vivo.

The positioning of the analyte monitoring devices in the body is typically accomplished with the aid of an insertion device, or inserter, that includes a sharp for penetrating the skin and allowing simultaneous or subsequent placement of the sensor within the resulting skin puncture. Conventional inserters can be bulky and/or complex devices that are expensive to manufacture and burdensome to use. These complex inserters are typically stored in sterile packaging and are not reusable, thus increasing the costs for the consumer. Furthermore, many typical inserters require some degree of assembly prior to use, either assembly of the inserter or the sensor device to be placed on and in the body, or both.

Thus, with the continued development of analyte monitoring devices and systems, there is a need for improved inserters that, for example, are more compact, less complex, easier to use, and cheaper to manufacture.

SUMMARY

Provided herein are example embodiments of improved medical device inserters, systems incorporating the same, and related methods of use. The inserter embodiments can be used in a wide variety of medical device applications, one example of which is for the insertion of analyte monitoring devices into the human body. While the inserter embodiments will be described herein with reference to an example analyte monitoring application, these embodiments are not limited to only that application.

Other systems, devices, methods, features and advantages of the subject matter described herein will be or will become apparent to one with skill in the art upon examination of the following figures and detailed description. It is intended that all such additional systems, devices, methods, features and advantages be included within this description, be within the scope of the subject matter described herein, and be protected by the accompanying claims. In no way should the features of the example embodiments be construed as limiting the appended claims, absent express recitation of those features in the claims.

BRIEF DESCRIPTION OF THE FIGURES

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be depicted schematically rather than literally or precisely.

FIG. 3C is a side view, rotated by 90 degrees from the view of FIG. 3A, depicting an example embodiment of the inserter and the sensor control device.

FIG. 3D is a cross-sectional perspective view of the example embodiment of the inserter and the sensor control device taken along line 3D-3D of FIG. 3C.

FIG. 4A is a side view depicting an example embodiment of an inserter and a sensor control device in a second stage of operation.

FIG. 4B is a cross-sectional perspective view of the example embodiment of the inserter and the sensor control device taken along line 4B-4B of FIG. 4A.

FIG. 4C is a side view, rotated by 90 degrees from the view of FIG. 4A, depicting an example embodiment of the inserter and the sensor control device.

FIG. 4D is a cross-sectional perspective view of the example embodiment of the inserter and the sensor control device taken along line 4D-4D of FIG. 4C.

FIG. 5A is a side view depicting an example embodiment of an inserter and a sensor control device in a second stage of operation.

FIG. 5B is a cross-sectional perspective view of the example embodiment of the inserter and the sensor control device taken along line 5B-5B of FIG. 5A.

DETAILED DESCRIPTION

Before describing this medical device inserter subject matter in greater detail, it is worthwhile to describe example embodiments of systems, devices, and methods with which this subject matter can be implemented.

A number of systems have been developed for the automatic monitoring of the analyte(s), like glucose, in bodily fluid such as in the blood stream, in interstitial fluid ("ISF"), dermal fluid of the dermal layer, or in other biological fluid. Some of these systems are configured so that at least a portion of a sensor is positioned below a skin surface of a user or recipient, e.g., in a blood vessel or in the dermal or subcutaneous tissue of a user, to obtain information about at least one analyte of the body.

Figure 1:
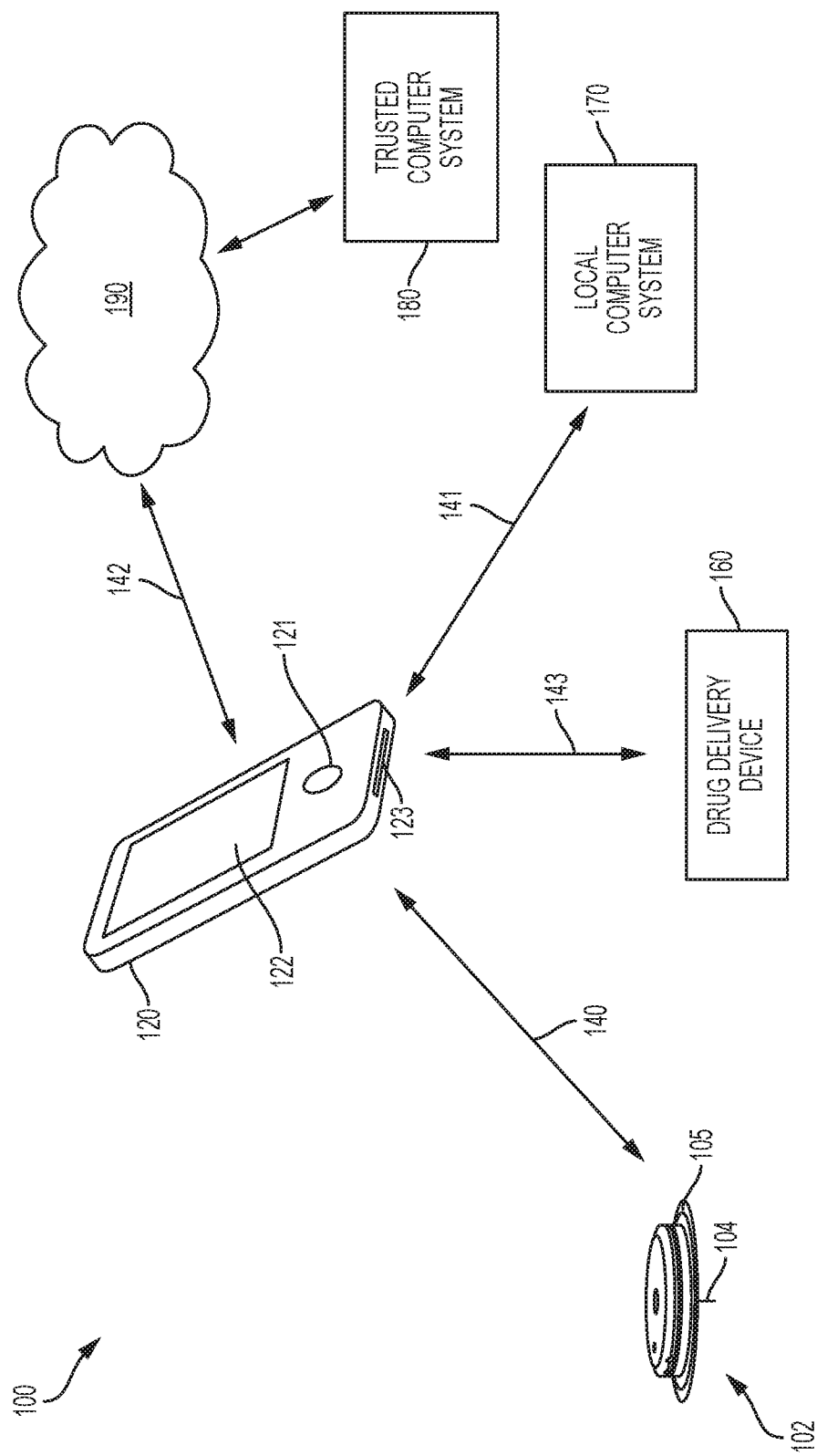
FIG. 1 is a high level diagram depicting an example embodiment of an analyte monitoring system for real time analyte (e.g., glucose) measurement, data acquisition and/or processing.

As such, these systems can be referred to as "in vivo" monitoring systems. FIG. 1 is a high-level diagram depicting an example embodiment of an in vivo analyte monitoring system 100, which in some embodiments can be a "Continuous Analyte Monitoring" system (or "Continuous Glucose Monitoring" (CGM) system) that can broadcast data from a sensor control device 102 having an in vivo sensor 104 to a reader device 120 continuously without prompting, e.g., automatically according to a broadcast schedule. System 100 can also (or alternatively) be configured as a "Flash Analyte Monitoring" system (or "Flash Glucose Monitoring" system or simply "Flash" system) that can transfer data from sensor control device 102 in response to a scan or request for data by reader device 120, such as with an Near Field Communication (NFC) or Radio Frequency Identification (RFID) protocol. Some embodiments of system 100 can also operate without the need for finger stick calibration.

In addition to CGM and Flash, system 100 can also be used with other types of in vivo analyte monitoring configurations.

The in vivo analyte monitoring system 100 can be differentiated from "in vitro" systems that contact a biological sample outside of the body (or rather "ex vivo") and that typically include a meter device that has a port for receiving an analyte test strip carrying bodily fluid of the user, which can be analyzed to determine the user's blood sugar level. While in many of the present embodiments the monitoring is accomplished in vivo, the embodiments disclosed herein can be used with in vivo analyte monitoring systems that incorporate in vitro capability, as well has purely in vitro or ex vivo analyte monitoring systems.

Sensor 104 can be part of the sensor control device 102 that resides on the body of the recipient and that contains the electronics and power supply that enable and control the analyte sensing. Sensor control device 102, and variations thereof, can also be referred to as a "sensor control unit," an "on-body electronics" device or unit, an "on-body" device or unit, or a "sensor data communication" device or unit, to name a few.

Reader device 120 can receive sensed analyte data from sensor control device 102 and processes and/or displays that sensed analyte data, in any number of forms, to the user. This device and variations thereof can be referred to, for example, as a "reader device" (or simply a "reader"), "handheld electronics" (or a handheld), a "portable data processing" device or unit, a "data receiver," a "receiver" device or unit (or simply a receiver), or a "remote" device or unit.

Sensor control device 102 and/or reader device 120 can each be configured to communication with a drug delivery device 160 that is capable of injecting or infusing a drug, such as but not limited to insulin, into the body of the individual wearing sensor control device 102. Sensor control device 102, reader device 120, and drug delivery device 160 can each be configured to communicate with a local or remote computer system 170 (such as a personal or laptop computer, a tablet, or other suitable data processing device) and/or with a remote trusted computer system 180 (which can include one or more computers, servers, networks, databases, and the like).

Additional detail regarding these and other example embodiments of in vivo monitoring systems 100 is provided in the following sections.

Embodiments of Medical Device Inserters

FIGS. 2A-7D depict example embodiments of an inserter or insertion device 200. Generally, these embodiments of inserter 200 have a compact design that is simpler and less burdensome to use, and less costly to manufacture than conventional inserters. Inserter 200 can be adapted for inserting at least a portion of sensor 104 into a recipient's body (e.g., that of a patient or human subject) and/or for placing sensor control device 102 on the recipient's body. For example, sensor 104 is inserted through the outer skin surface of the recipient until one or more electrodes on sensor 104 are placed into contact with a bodily fluid (e.g., blood, interstitial fluid, dermal fluid of the dermal skin layer, etc.) where those electrodes can reside for use in sensing an analyte level of the recipient.

In another embodiment, insertion device 200 can be used with a medical device having a drug infusion (e.g., insulin) cannula, where insertion device 200 applies the device to the body of a recipient such that the drug infusion cannula is inserted into the body of the recipient with the aid of a sharp. In certain embodiments, this medical device can also include sensor control device 102 (or at least analyte sensor 104, which may be separate from the cannula such that two sharps are used to create two body punctures, or analyte sensor 104 may be integrated with or attached to the cannula such that both sensor 104 and the cannula are inserted into the same body puncture with the aid of the same sharp).

The operator performing the insertion process with inserter 200 can be the same individual as the recipient of sensor 104, or the operator and recipient can be different individuals. Whether the same or different, both the operator and recipient are users of inserter 200. Both can also be users of system 100, or components thereof.

Figure 2B:
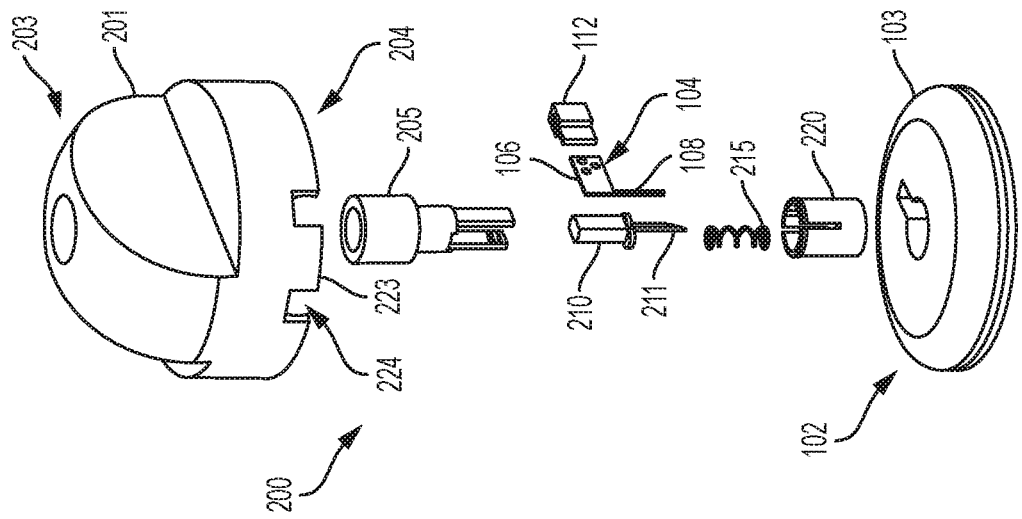
FIGS. 2A and 2B are exploded bottom up and top down perspective views, respectively, depicting an example embodiment of an inserter and sensor control device.
Figure 2A:
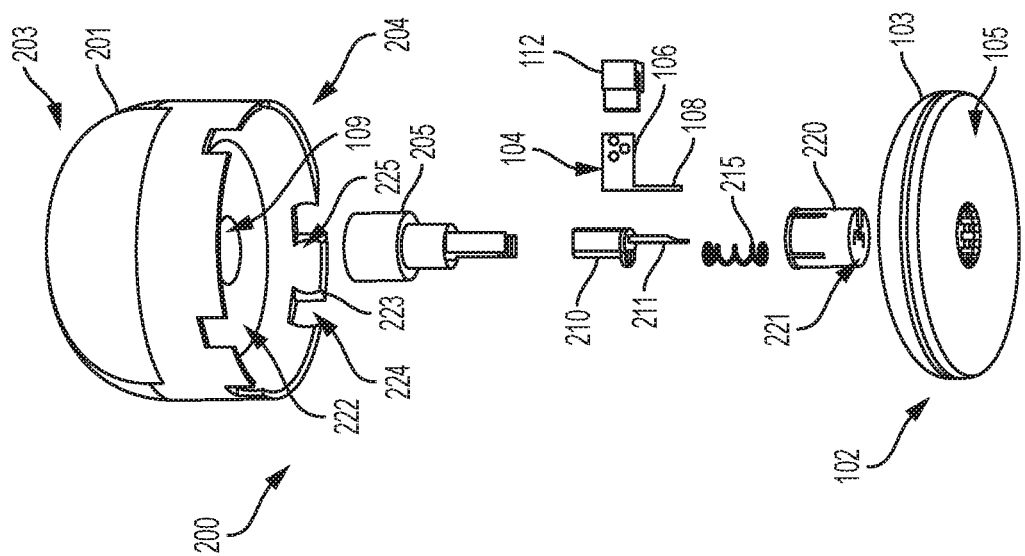

FIGS. 2A and 2B are exploded assembly views, from a bottom perspective and top perspective, respectively, depicting an example embodiment of inserter 200 for use with sensor control device 102. As shown here, inserter 200 can include a housing 201 that can also be configured as a handle for the operator. Housing 201 has a posterior side 203 and an anterior side 204. A relatively wider or flared section 202 with a recess 222 for receiving and holding housing 103 of sensor control device 102 is located on the anterior side 204 of housing 201. Inserter 200 can further include a sharp support 205, a sharp body 210 coupled to sharp 211, a biasing element 215, and a shroud 220.

The relative terms "posterior" and "anterior" are used herein to denote the back and front of the device, respectively, where the anterior side is the side placed against the recipient's skin from which sensor 104 is deployed, and the opposite side is the posterior side that is generally held in the operator's hand. As used herein, the term "advancement" in its various forms generally refers to motion in a posterior to anterior direction, and the term "retraction" in its various forms generally refers to motion in an anterior to posterior direction.

Sharp body 210 can slidably receive sensor 104, which in turn can be coupled with sensor control device housing 103 by way of a sensor mount 112. Sensor control device 102 can be releasably coupled with inserter 200 in a number of different manners. For example, one or more deflectable elastic projections, snaps, clips, or shaped contours can be used to mechanically engage with housing 103 of sensor control device 102. The attachment mechanism can be self-releasing or can include an actuator mechanism (e.g., a trigger, lever, switch, and the like) to allow a user to manually unlock sensor control device 102 from housing 201. In the embodiment described with respect to FIGS. 2A-B, three deflectable arms 223 are spaced evenly about the anterior periphery of housing 201 with gaps 224 on both sides. These arms 223 project anteriorly and can have a contoured inner surface 225 that is complementary to the shape of sensor housing 103. For example, in this embodiment sensor housing 103 has a rounded convex outer surface and inner surface 225 has a matching concave shape.

In many embodiments it is desirable that sensor control device 102 be released from inserter 200 by pulling inserter 200 away from the user's body (i.e., posteriorly) after attaching sensor control device 102 to the user's skin, such as with adhesive layer 105. Thus the posteriorly directed force necessary to release sensor control device 102 from inserter 200 should be less than the force at which sensor control device 102 is detached from the user's body. Thus, for example, contoured surface 225 on the interior of each arm 223 provides a coupling mechanism that can be released with the exertion of a relatively low pulling force, as compared to standard mechanical catches with detents. In other embodiments, sensor control device 102 can be attached to inserter 200 with a low tack adhesive or with the use of one or more magnetic elements (e.g., a magnet on sensor control device 102 and/or a magnet on inserter 200, each adapted to attract another magnet or ferromagnetic material on the opposite structure).

As can be seen in FIGS. 2A-B, sensor 104 can include a posterior portion 106 from which extends an anterior projection 108 adapted for at least partial insertion into the recipient's body. Sensor projection 108 can include three electrodes (not shown) for electrochemically sensing the user's analyte level. In other embodiments, sensor 104 can include one or more electrodes. These electrodes are electrically connected to electrical contacts 107 on proximal portion 106. Contacts 107 can overlie and be placed in electrical contact with opposing contacts (not shown) in sensor control device 102, which are in electrical communication with the circuitry of device 102 that is responsible for electrically controlling sensor 104 and monitoring the electrical signals produced on the sensor electrodes in response to the detection of the analyte (e.g., glucose).

FIGS. 3A-5E depict an example embodiment of inserter 200 at various stages of operation and will be used to describe inserter 200 in greater detail. To apply sensor control device 102 and insert sensor 104 into the user's body, in many embodiments, while shroud 220 is fully or mostly extended from sensor control device 102, an anterior surface 221 (described below) of shroud 220 is placed against the skin of the user at the desired implantation site (e.g., the upper arm or lower back). FIGS. 3A-F depict inserter 200 at this first stage of operation where shroud 220 is fully or mostly extended. Housing 201 can then be advanced relative to shroud 220 in order to advance at least a portion of sensor projection 108, along with sharp 211, from shroud 220 into and through the skin and into the body of the recipient. FIGS. 4A-E depict inserter 200 at a second stage of operation where shroud 220 has been partially retracted from the fully extended position, exposing sharp 211 and sensor projection 108.

Upon fully advancing housing 201 against the user's body, adhesive layer 105 of sensor control device 102 contacts and engages with the user's skin. Shroud 220 is fully (or mostly retracted) and sharp 211 and sensor projection 108 are advanced to the desired depth in the user's body. FIGS. 5A-E depict inserter 200 at this third stage of operation where shroud 220 has been fully or mostly retracted. At this point, sharp body 210 (along with sharp 211) can be released by internal components of inserter 200 and automatically retracted by biasing element 215 to a retracted position as discussed in further detail hereinafter. Inserter 200 can then be removed from the user's body and sensor control device 102 released from inserter 200 and left behind in position to monitor the user's analyte levels.

Referring back to the first stage of operation, FIGS. 3A-F depict inserter 200 with shroud 220 fully or mostly extended. Here, inserter 200 is shown in a loaded state coupled with sensor control device 102. With shroud 220 extended as shown, inserter 200 is ready to insert sensor 104 into the recipient's body and apply sensor control device housing 103 to the recipient's skin by way of adhesive layer 105. As will be described in more detail below, sharp 211 is positioned in close proximity with sensor projection 108 (FIGS. 3B, 3D) such that sharp 211 can create a puncture in the user's body and guide sensor projection 108 into the user's body. Sharp 211 is movable with respect to projection 108 and can be withdrawn from the user's body while leaving sensor projection 108 implanted therein.

In many embodiments, in the extended position, shroud 220 covers sharp 211 and sensor projection 108 thereby protecting users from sharp 211, and protecting sharp 211 and sensor projection 108 from external damage and/or contamination. Shroud 220 can include an anterior opening 276 (FIG. 3D, 3E), that may be the terminus of an interior lumen 277 (FIG. 3D, 7C), through which sharp 211 and sensor projection 108 can pass.

In the embodiments depicted, shroud 220 is a cylindrical or substantially cylindrical housing. Those of ordinary skill in the art, upon reading this description, will readily recognize those structures that are "substantially cylindrical," as such structures are not limited to a pure geometric cylinder but include all variations of cylinder shapes, including those that are polygonal in cross-section, tapered, at least partially conical, hourglass-like, and so forth. Shroud 220 can also have a non-cylindrical shape that acts as a retractable cover or shield for one or both of sharp 211 and sensor projection 108.

Shroud 220 can be held in the extended position relative to device 102 by a lock mechanism 234 that engages shroud 220 with sensor control device 102. An embodiment of lock mechanism 234 is depicted, for example, in FIG. 3D. Here, lock mechanism 234 is implemented with a detent 235 that can extend radially outwardly from shroud 220 and engage with a corresponding recess 135 in device 102, which in this embodiment is formed between radially inwardly extending detents 136 and 137. Recess 135 and detents 136 and 137 are formed in sensor housing 103 (see also FIG. 6B), although these elements can be formed elsewhere on device 102. When detents 235 of shroud 220 are releasably engaged with recess 135 of sensor housing 103, shroud 220 is mechanically held in its position relative to sensor control device 102. It should be noted that all of the various detents described herein can also be implemented as a projection or an extending member.

Figure 3B:
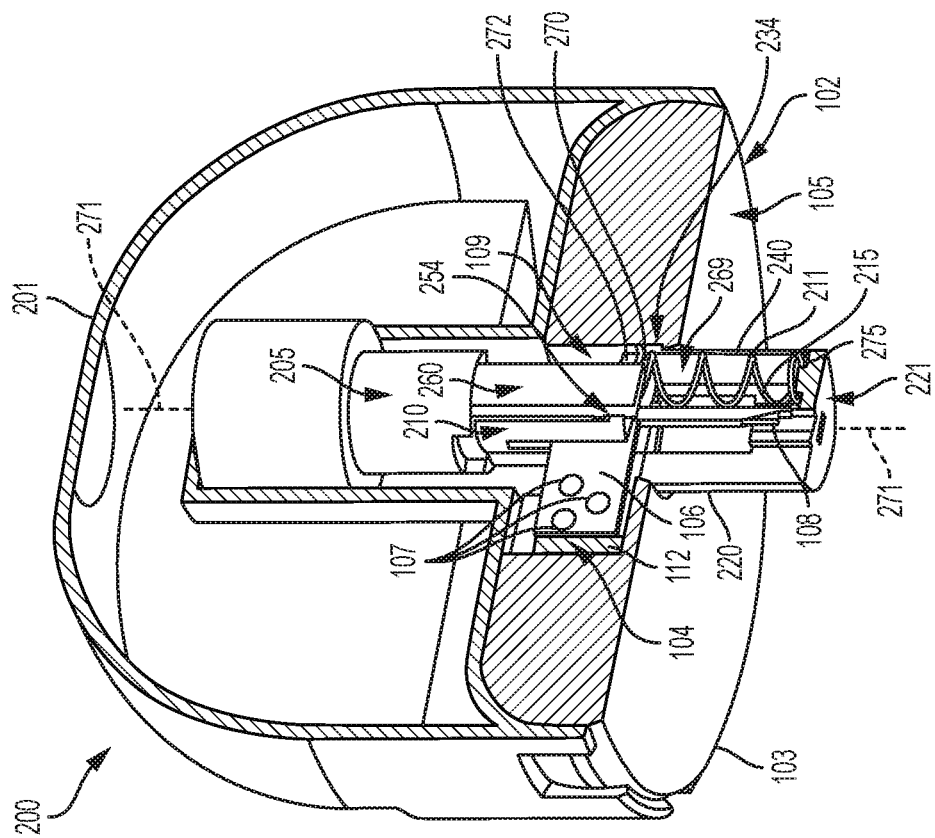
FIG. 3B is a cross-sectional perspective view of the example embodiment of the inserter and the sensor control device taken along line 3B-3B of FIG. 3A.
Figure 3A:
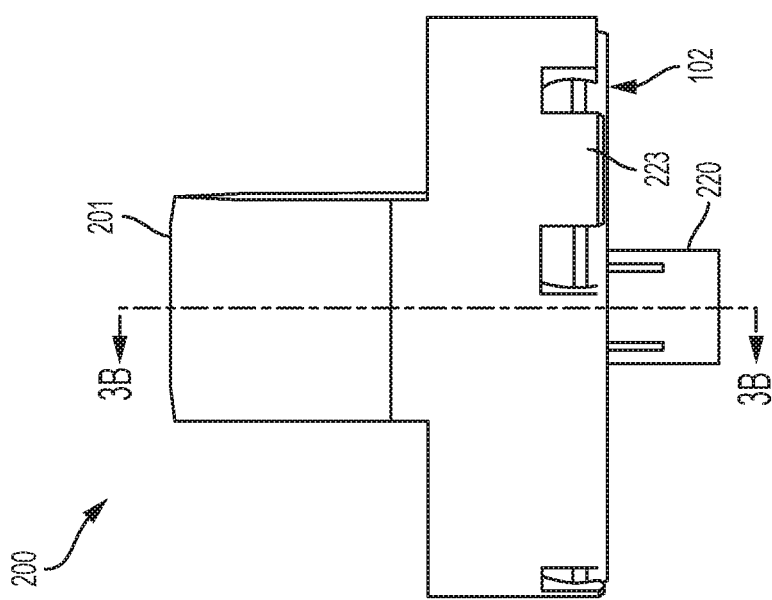
FIG. 3A is a side view depicting an example embodiment of an inserter and a sensor control device in a first stage of operation.
Figure 3F:
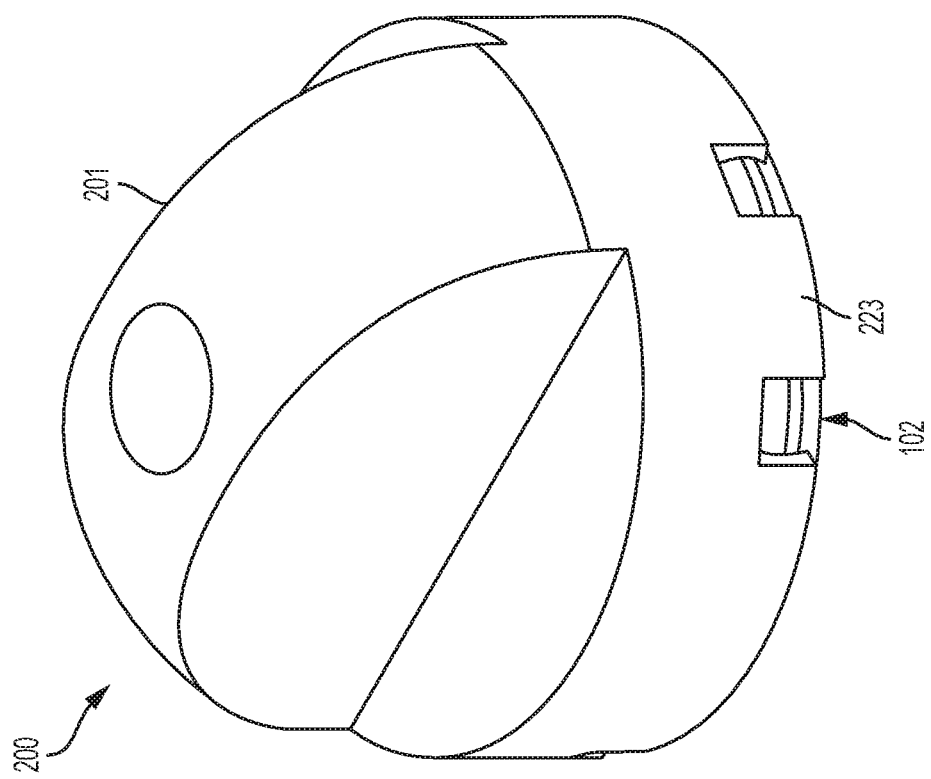
FIGS. 3E and 3F are bottom up and top down perspective views, respectively, of an example embodiment of the inserter and the sensor control device.
Figure 3E:
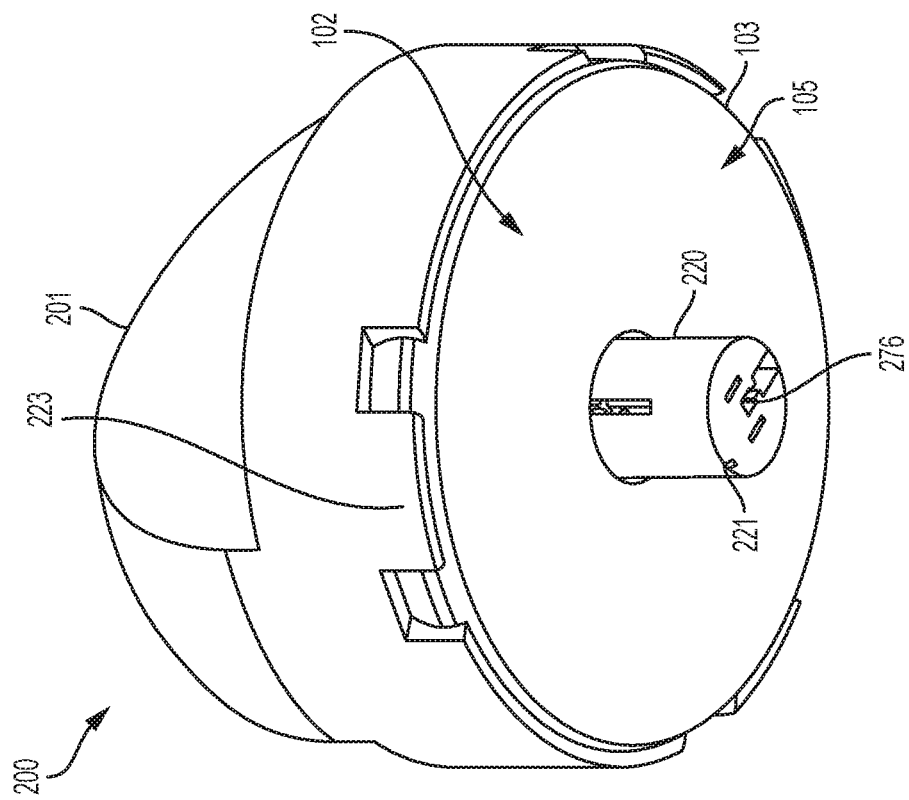
Figure 4E:
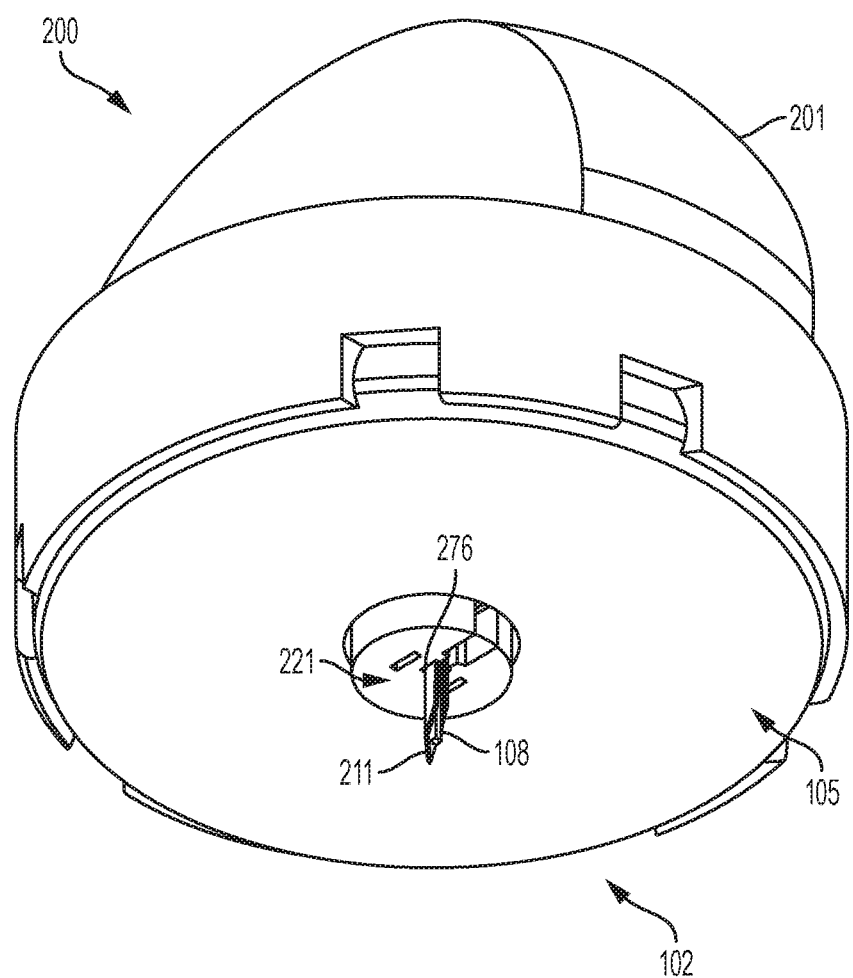
FIG. 4E is a bottom up perspective view of an example embodiment of the inserter and the sensor control device.

Each detent 235 can be coupled with an elastic support 240 that is biased towards the position shown in FIGS. 3B, 3D, and 4D. Here, elastic support 240 is configured as an elastic arm and detent 235 (FIG. 3D) is integrally formed along the end of elastic arm 240 as a ledge that projects radially outwardly. Multiple elastic arms 240 can be present about the periphery of shroud 220, as described with respect to FIGS. 7C-D. Each detent 235 can be releasably maintained in recess 135 by elastic arm 240, which is deflectable inwardly from this position to allow disengagement of detent 235 from recess 135, and in turn to allow disengagement of shroud 220 from sensor housing 103. Alternatively, recess 135 can be implemented as a single groove that extends around substantially all of the periphery of sensor housing 103.

In other embodiments, the structures that form lock mechanism 234 can be reversed. For example, at least one recess or groove can be present on each elastic support 240 instead of a detents 235, and each such recess or groove can engage with a complementary detent or projection on sensor control device 102 or housing 103, similar to detent 136 or 137.

Angled surfaces can be present on detents 136, 137, and 235 and any portion of the other releasable lock mechanisms described herein in order to facilitate releasable engagement. The angle of these surfaces can be varied to obtain the desired resistance to engagement and/or disengagement. Angling of contact surfaces can facilitate translation of longitudinal motion (e.g., posterior-anterior motion) of one structure, e.g., the main body of shroud 220, into lateral motion (e.g., sideways motion) of another structure, e.g., elastic arms 240.

When anterior surface 221 of shroud 220 is placed against the recipient's body and sufficient force is applied to housing 201 in a direction towards the recipient's body, detents 235 will release from recess 135 and allow shroud 220 to retract into an opening 109 (FIG. 3B) within sensor control device 102. Thus, lock mechanism 234 can be released upon application of a predetermined manual force by the user.

Referring to FIG. 3B, inserter 200 can also include a second lock mechanism 254 that can releasably couple sharp support 205 with sharp body 210. Lock mechanism 254, which is shown in more detail in the embodiment depicted in FIG. 7A, can be implemented with one or more detents 255 and complementary recesses or grooves 256. Each detent 255 can radially outwardly extend from sharp body 210. Each detent 255 can be received within recess or groove 256 in sharp support 205. In this embodiment, recess 256 is formed by the space between optional projections 257 and 258, which extend radially inwardly from sharp support 205. More particularly, projections 257 and 258 extend from elastic supports 260 that, in this embodiment, are configured as elastic arms.

Any number of one or more elastic arms 260 can be utilized. In this embodiment, two elastic arms 260 are present, each in a position that opposes the other (e.g., present on opposite sides of sharp body 205). In some embodiments, sharp support 205 is a discrete component coupled with housing 201. In other embodiments, housing 201 and sharp support 205 are integral, e.g., molded from a single polymer. In either case, elastic arms 260 can be considered as coupled with housing 201.

Each recess 256 can be releasably maintained over detent 255 by elastic arm 260 to lock or secure sharp body 210 in position with respect to sharp support 205. Each elastic arm 260 is biased towards and deflectable outwardly from the position shown in FIGS. 3B and 7A to allow disengagement of recess 256 from detent 255, and in turn to allow disengagement of sharp body 210 from sharp support 205. One or more elastic arms 260 can be present and positioned as desired about the periphery of sharp support 205 to adequately engage and hold sharp body 210. Alternatively, and as described with respect to lock mechanism 234, the arrangement of lock mechanism 254 can be reversed such that recess 256, and projections 257 and 258 if present, are instead on sharp body 210 and detent 255 is on elastic arm 260.

Shroud 220 comprises a release mechanism 265 configured to unlock lock mechanism 254 and uncouple sharp support 205 from sharp body 210. In this embodiment, release mechanism 265 is a projection that extends away from surface 221 towards sharp support 205 when shroud 220 is in the extended position depicted in FIG. 3D. Release mechanism 265 can have an angled, rounded, beveled, or chamfered surface 266 that is positioned to contact an anterior surface 267 of arm 260, which can also be angled, rounded, beveled, or chamfered in a complementary (e.g., opposite) fashion. Retraction of shroud 220 causes surfaces 266 and 267 to contact (as will be described with respect to FIG. 4D) and translate the retracting force into a lateral or radially outward motion of arms 260, which in turn disengages each recess 256 from its respective detent 255 and release sharp body 205 from sharp support 210.

Biasing element 215 (FIGS. 3B, 4B, 5B; also referred to as a "bias" element) can be any structure or medium that can apply a bias or force to sharp body 205 and cause sharp body 205 to retract from the extended or advanced shroud position depicted in FIG. 3B. In the embodiments described herein, biasing element 215 is a helical coil spring, however other spring shapes can be used as well. Also, biasing element 215 can be configured as a structure that relies upon other media such as gas or fluid for the application of a retraction force.

Referring back to FIG. 3B, when shroud 220 is in the extended position, biasing element 215 is held in a relatively uncompressed state in an open chamber 269 within shroud 220. Biasing element 215 is laterally offset from a central axis 271 of inserter 200 and acts against two opposing surfaces 270 and 275, both of which can surround semi-cylindrical projections that can be received within the central lumen space of the helical coil and prevent the coil from sliding substantially out of position within chamber 269. In other embodiments, a center longitudinal axis of biasing element 215 can be aligned with central axis 271 of inserter 200. For example, a biasing element 215 configured as a helical coil spring can surround sharp 211 and sensor projection 108 such that the axis of withdrawal of sharp 211 can be within the central lumen of the helical spring along its central axis (generally the same position as central axis 271). The alignment of the axis of withdrawal of sharp 211 and the central axis of biasing element 215 can minimize the exertion of torque or a lateral moment on sharp body 205 during withdrawal.

Surface 270 faces anteriorly and is present on an extension or ledge 272 of sharp body 210 that is offset and extends away from sharp 211. This extension 272 is sized to fit and slide longitudinally within chamber 269, which has an open side to allow the extension's passage. Surface 275 faces posteriorly and is present on the anterior side of shroud 220, also in a position that is offset from sharp 211 itself.

The posterior side of sharp support 205 has a relatively large cylindrical portion that is coupled with an interior channel of housing 201, as shown in FIGS. 3B and 3D, and fixes sharp support 205 in place with respect to housing 201. Sharp support 205 may be coupled with housing 201 by a mechanical attachment such as welding, adhesive bonding, a snap or clip, a bayonet mount, an interference fit, or in another suitable manner that would allow it to be permanently or removably attached. As stated, sharp support 205 may also be formed as part of the housing such that they are one continuous component (e.g., monolithic).

Reference is now made to the second stage of operation, described with respect to FIGS. 4A-E, and the third stage of operation, described with respect to FIGS. 5A-E. The pressing of anterior shroud surface 221 against the skin (by the application of an anteriorly directed force by the user upon housing 201, i.e., pushing inserter 200 against the skin) causes shroud 220 to begin to retract upon disengagement of lock mechanism 234. Shroud 220 is shown in a partially retracted state in FIGS. 4A-E. The continued pressing of surface 221 against the skin causes shroud 220 to fully retract as shown in FIGS. 5A-E.

Because sharp support 205 is held in place by housing 201, and because sharp body 210 is held in place with respect to sharp support 205 by lock mechanism 254, the retraction of shroud 220 causes sharp 211 to pass through lumen or channel 277 (FIGS. 3D, 7C) and emerge from aperture 276 (FIG. 4B) in shroud 220. The retraction of shroud 220 also compresses biasing element 215 such that it transitions from a relatively uncompressed state to a relatively compressed state (FIG. 4B).

The continued retraction of shroud 220 causes release mechanism 265 to begin to disengage lock mechanism 254. As described earlier, the opposing angled or rounded surfaces 266 and 267 are pressed together (FIG. 4D) and the continued application of that force causes arms 260 to deflect outwards, disengaging recesses 256 from detents 255.

Upon disengagement of lock mechanism 254, sharp body 210 is no longer secured in place with respect to sharp support 205, and the pressure exerted by the now compressed biasing element 215 between surfaces 270 and 275 causes sharp body 210 to move posteriorly, i.e., to retract, into a space or cavity 278 (FIG. 5B) within sharp support 205. (Shroud 220 and surface 275 are prevented from moving anteriorly by the user's body.) This movement withdraws sharp 211 from the user's body without moving sensor 104, such that projection 108 remains fully extended (FIGS. 5A-E) in a position where the terminus of projection 108 would be at the desired depth within the user's body (e.g., within a dermal layer, subcutaneous layer, etc.).

In alternative embodiments, inserter 200 can be configured such that sharp 211 is manually withdrawn, e.g., the operator grasps sharp 211 and manually pulls it from the recipient's body. In other embodiments, sensor projection 108 can be configured, for example, with a sharp anterior terminus that pierces the user's body directly without the need for an additional sharp, thus also eliminating the need for withdrawal of an ancillary sharp.

Proximal portion 106 of sensor 104 can at least partially reside within an elongate opening or gap 279 in sharp body 210 (FIG. 4B). Elongate gap 279 can be shaped like a slit to allow sharp body 210 to slidably receive or pass over the planar-shaped proximal portion 206. When shroud 220 is retracted far enough to release lock mechanism 254, sharp body 210 is freed and forced posteriorly by biasing element 215. Sharp body 210 slides over sensor 104 into the fully retracted state (FIGS. 5B, 5D).

Figure 5D:
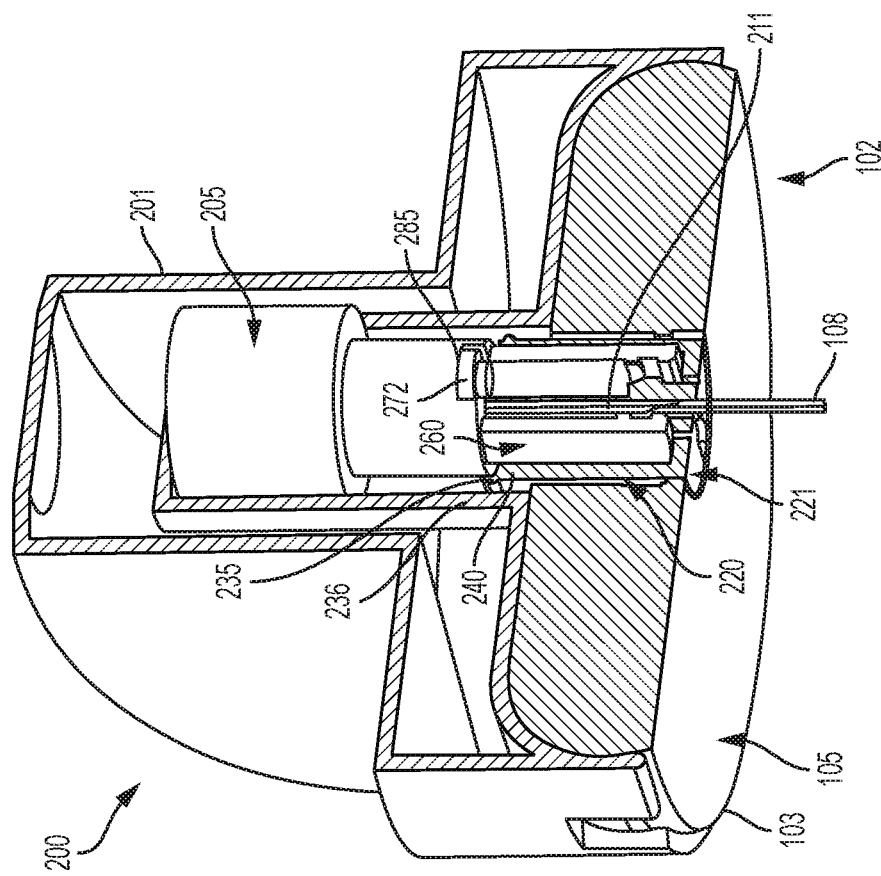
FIG. 5D is a cross-sectional perspective view of the example embodiment of the inserter and the sensor control device taken along line 5D-5D of FIG. 5C.
Figure 5C:
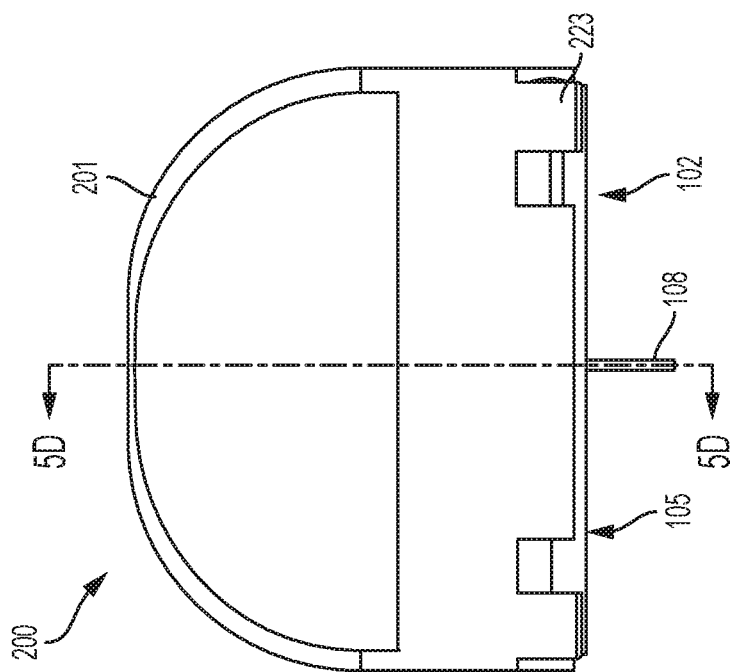
FIG. 5C is a side view, rotated by 90 degrees from the view of FIG. 5A, depicting an example embodiment of the inserter and the sensor control device.
Figure 5E:
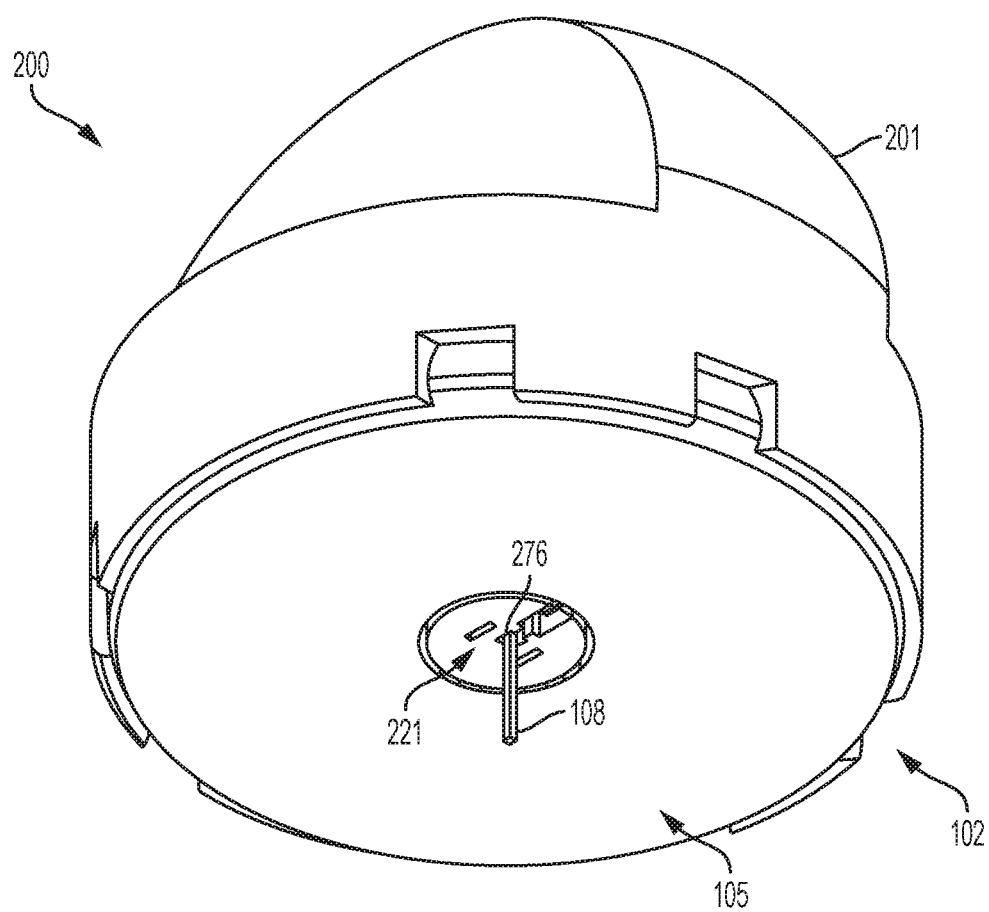
FIG. 5E is a bottom up perspective view of an example embodiment of the inserter and the sensor control device.

With reference to FIGS. 4D and 5D, sharp support 205 can include a stop 280 that is positioned so as to contact an opposing stop 285 on sharp body 210, which in this embodiment is the posterior surface of ledge 272. These opposing stops 280 and 285 define a position at which sharp body 210 is fully retracted and prevent further posterior motion of sharp body 210.

Biasing element 215 can cycle through three states during the insertion process. In the first state, shroud 220 is in the extended position and biasing element 215 is in a relatively uncompressed state (FIG. 3B). This relatively uncompressed state can be fully uncompressed or only partially compressed. In some embodiments, lock mechanism 234 can be omitted altogether and shroud 220 can be maintained in the extended proximal position by biasing element 215 itself in this first state.

As shroud 220 is retracted, biasing element 215 is compressed until shroud 220 reaches an intermediate position where shroud 220 is not yet fully retracted but the release of lock mechanism 254 is imminent (FIG. 4B). At this intermediate position biasing element 215 is in a second, relatively compressed state. In many embodiments, the amount of compression at this point is the maximum compression that biasing element 215 undergoes during the insertion process. Although when in a state of at least partial compression, biasing element 215 still exerts an expansive force against the surfaces that restrain it.

The intermediate position where sharp 211 begins retraction can be adjusted according the needs of the application and can be, for example, at the halfway distance between full extension of shroud 220 and full retraction of shroud 220 where shroud 220 is flush with surface 105 of sensor control device (FIGS. 5A-E). In other embodiments, the intermediate position can be relatively closer to the fully retracted position that the fully extended position of shroud 220, or vice versa. In some embodiments, lock mechanism 254 is released upon full retraction of shroud 220 such that the intermediate position and fully retracted position of shroud 220 are the same.

Once lock mechanism 254 is released, biasing element 215 begins to decompress from the relatively compressed state back towards a third relatively uncompressed state (FIG. 5B), which again may be fully uncompressed or partially compressed, either the same or different from the first state.

After reaching the fully retracted state, surface 221 of shroud can be generally flush with adhesive surface 105 of sensor control device 102 such that adhesive surface 105 is in contact with the recipient's skin. Once adequate adhesive contact is obtained, the operator can remove inserter 200 leaving sensor control device 102 behind on the recipient's body with sensor 104 at least partially in vivo.

In some embodiments, shroud 220 can be maintained or secured in the fully retracted position by a lock mechanism similar to those described herein, or otherwise. For example, upon reaching a fully retracted position, detent 235 of shroud 220 can enter a recess (not shown) on an inner surface of housing 201, such as inner wall 235 (FIG. 5D), and detent 235 can be maintained in that recess by the radially outward bias exerted by arms 240. In another embodiment, shroud 220 can be maintained in position solely by the friction between detent 235 and a smooth interior surface of inserter 200 (e.g., inner wall 235) that lacks a recess or other detent or catch.

Figure 6A:
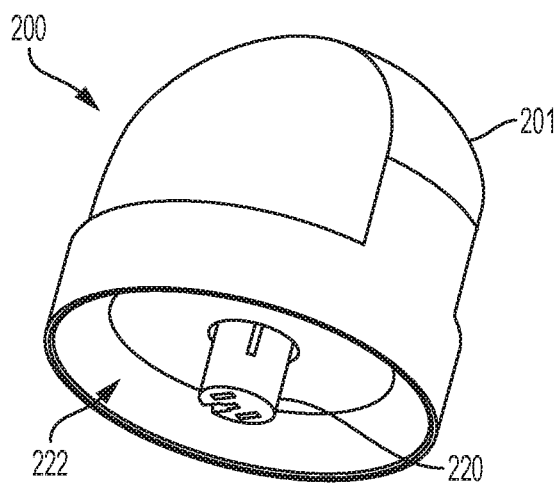
FIG. 6A is a perspective view depicting an example embodiment of an inserter.
Figure 6B:
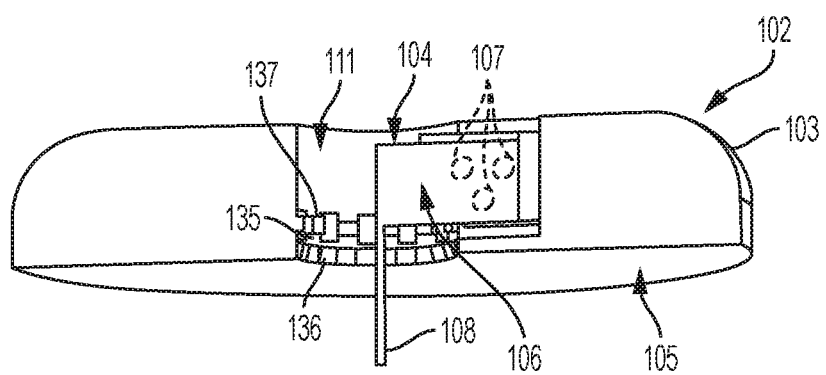
FIG. 6B is a cross-section view depicting an example embodiment of a sensor control device.

FIG. 6A is a perspective view depicting an example embodiment of inserter 200 after removal, with shroud 220 in the retracted position and open recess 222 where sensor control device 102 had been previously housed. In this embodiment, inserter 200 is adapted to retain sensor control device by a friction fit between shroud 220 and housing 103 within opening 111. FIG. 6B is a cross-sectional view depicting an example embodiment of sensor control device 102 after removal of inserter 200 (the recipient's body is not shown). Here, adhesive surface 105 would be in contact with the exterior of the recipient's skin and sensor projection 108 would be mostly implanted within the recipient's body. If sensor 104 is a dermal sensor, then the distance by which projection 108 would extend into the body can be less than the full depth of the dermal layer, so that the electrodes on projection 108 are primarily in contact with dermal fluid and not interstitial fluid (ISF).

Also shown here is generally cylindrical opening 111 which receives shroud 220, sharp body 210, and sharp support 205. Located around the periphery of opening 111 are multiple detents 136 and 137. In this embodiment, each detent 136 is offset from each detent 137 such that the two detents are not directly above or below each other. In other embodiments the detents can be aligned such that they are directly above and below each other. In still other embodiments, detent 136 and/or detent 137 can be in the form of a ridge or lip that extends partially or entirely around the periphery of opening 111. Detent 136 is relatively anterior to detent 137, and detent 136 resists, and in many instances prevents, detent 235 of shroud 220 from passing in a posterior to anterior direction, which prevents shroud 220 from being removed in that same direction.

Figures 6C, 6D:
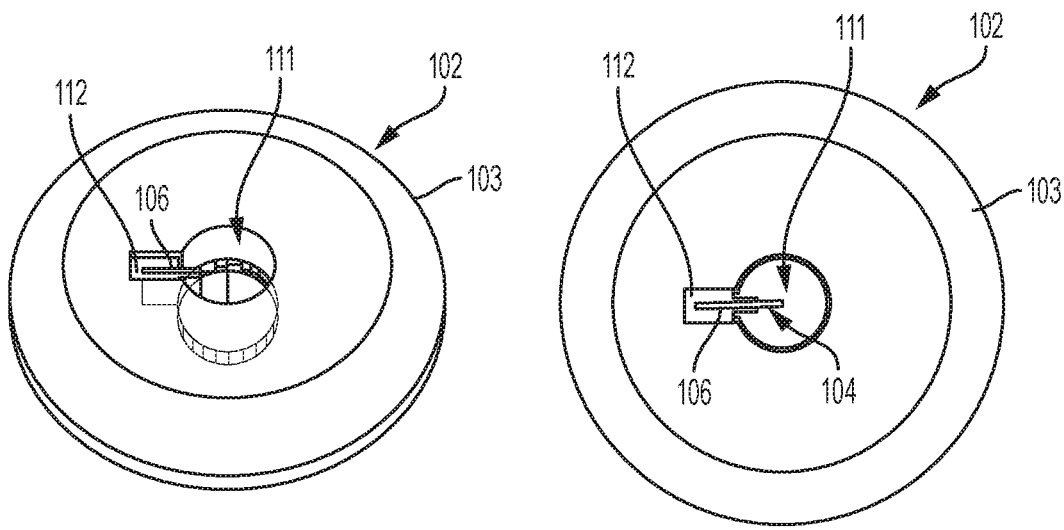
FIGS. 6C-D are perspective and top-down views, respectively, depicting an example embodiment of a sensor control device.

FIGS. 6C-D are top-down perspective and top-down views, respectively, of sensor control device 102 after removal of inserter 200. Here, a mount, support, or coupling 112 secures proximal portion 106 of sensor 104 to sensor control device 102. Mount 112 can include electrical connections to contacts 107 (not shown) on proximal portion 106. While sensor projection 108 is shown extending generally from the center of opening 111, in other embodiments projection 108 can be positioned adjacent the sidewall of opening 111.

In other embodiments, some or all of the inserter 200 may remain with sensor control device 102 on the recipient. For example, in some embodiments the recipient can wear the inserter for the entire lifetime of the sensor control device 102. In those cases, inserter 200 can be configured with a lower profile so as to minimize its noticeability. In other embodiments, housing 201 is removed but shroud 22, sharp 210, and sharp support 205 remain with sensor control device 102. In yet other embodiments housing 201, sharp 210, and sharp support 205 are removed but shroud 220 remains with device 102.

Figure 7A:
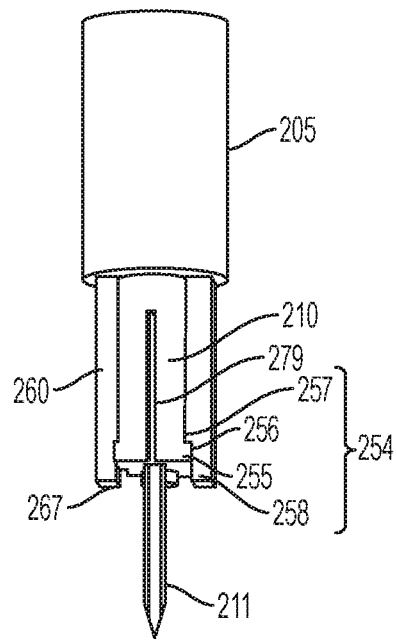
FIG. 7A is a side view depicting an example embodiment of a sharp support and a sharp body.
Figure 7B:
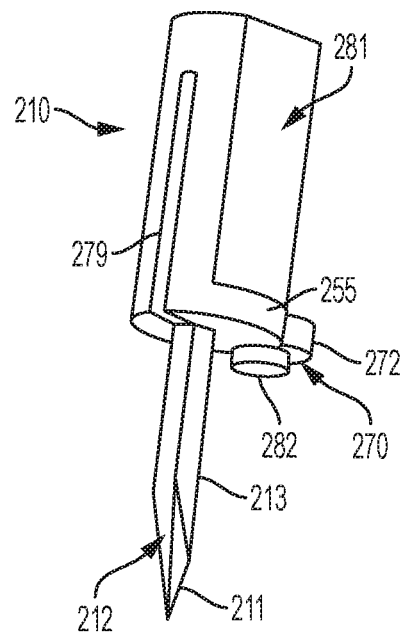
FIG. 7B is a perspective view depicting an example embodiment of a sharp body.

FIG. 7A is a side view depicting an example embodiment of sharp body 210 coupled with sharp support 205. FIG. 7B is a perspective view of an example embodiment of sharp body 210. In this embodiment, sharp 211 has a U-shaped configuration where opposing sidewalls 213 form a channel 212 therebetween. Sensor projection 108 (not shown) can reside within channel 212 such that sharp 211 can partially surround and protect sensor projection 108 during the insertion process. Also in this embodiment, detent 255 is configured as a rounded ledge that projects from a posterior mount 281 that is fastened to sharp 211. Elongate gap 279 is located within this posterior mount 281. A semi-cylindrical projection 282 is positioned on ledge 272 for engaging with an inner lumen of a helical spring biasing element 215 (not shown).

Figure 7C:
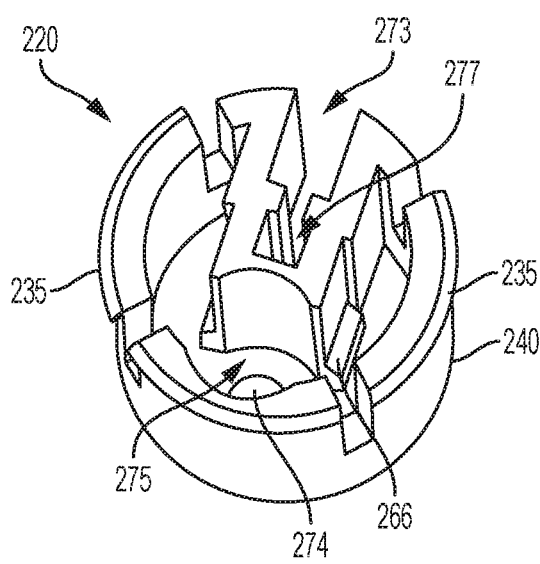
FIGS. 7C-D are top-down and bottom-up perspective views, respectively, depicting an example embodiment of a shroud.
Figure 7D:
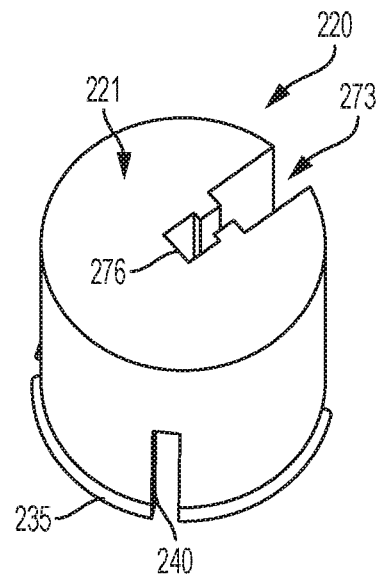

FIGS. 7C and 7D are top and bottom perspective views, respectfully, depicting an example embodiment of shroud 220. Although any number of one or more elastic arms 240 can be utilized, in this embodiment, shroud 220 includes three elastic arms 240, each with detent 235 in the form of a projecting ledge or lip. Release surface 266 for releasing elastic arms 240 has an angled or beveled configuration different from the embodiment shown in FIGS. 3D and 4D. Also shown is an elongate gap or opening 273 to allow the passage of planar proximal portion 106 of sensor 104 (not shown). A semi-cylindrical projection 274 is positioned near surface 275 for engaging with an inner lumen of a helical spring biasing element 215 (not shown).

Although not shown, to assist in guiding advancement and/or retraction of shroud 220, one or more elongate grooves, spaces, or channels can be implemented in which a projection or extension can slide. For example, the elongate groove, space, or channel can be present in shroud 220 with the longitudinal axis of that groove, space, or channel generally aligned with the direction of sliding motion, such that a projection or extension on the interior of housing 201 can be received into the groove, space, or channel and thereby guide the motion of shroud 220, preventing shroud 220 from rotating or tilting during advancement and/or retraction. Alternatively, the projection or extension can be present on shroud 220 and can be received in a groove, space, or channel in housing 201 with similar effect.

Figure 8:
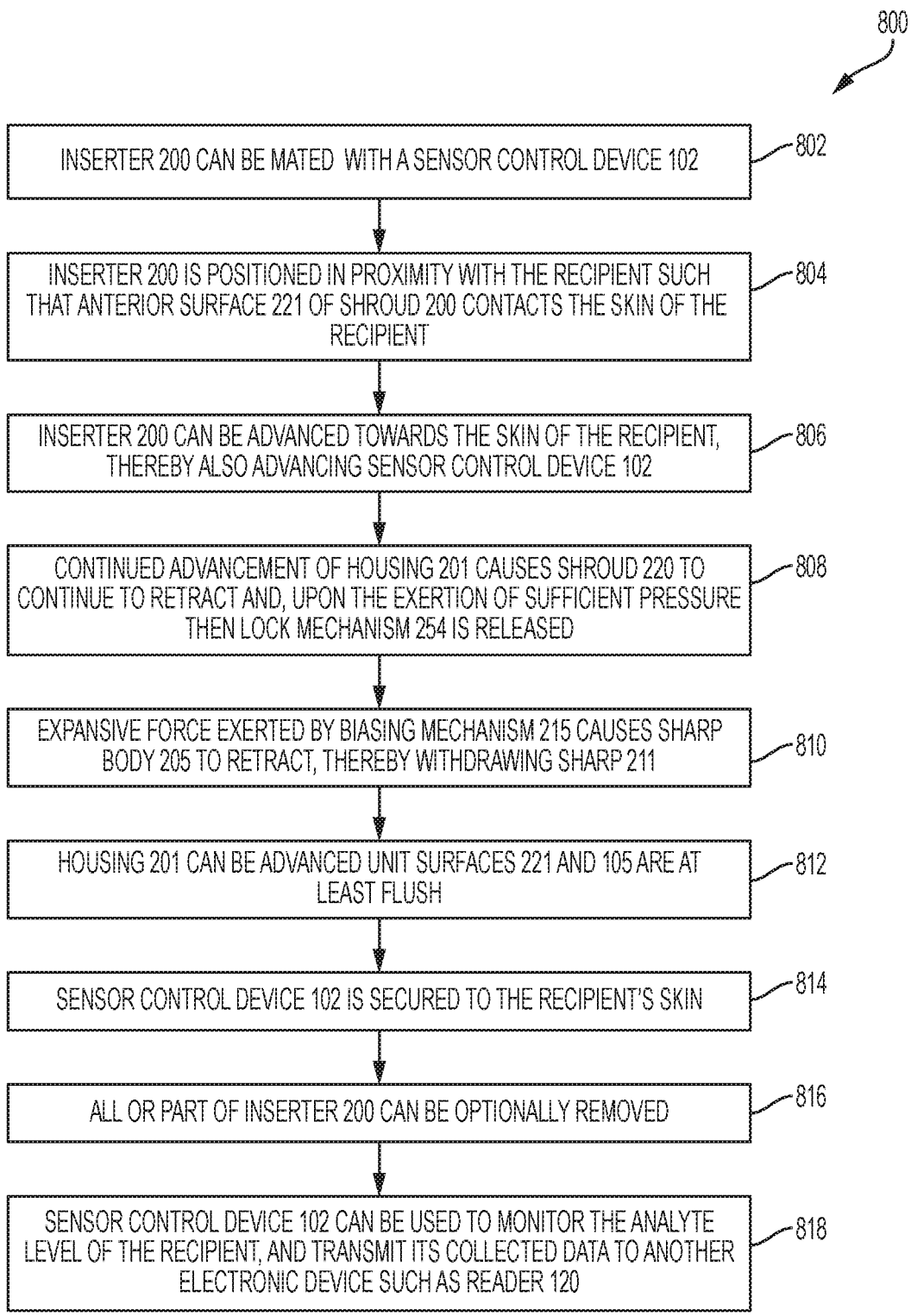
FIG. 8 is a flow diagram depicting an example embodiment of a method of using example embodiments of an inserter.

FIG. 8 is a flow diagram depicting an example method 800 of using certain embodiments of inserter 200 described herein. Inserter 200 and sensor control device 102, along with their various components, are described but not shown in FIG. 8, as these structures and their variants are shown in detail with respect to FIGS. 2A-7B.

At 802, inserter 200 can be mated with a sensor control device 102. This can be performed during manufacturing or by the user after distribution thereto. At 804, in a state where shroud 220, sharp 211, and sensor projection 108 are extended from an anterior surface 105 of sensor control device 102 and also where sharp 211 and sensor projection 108 are covered by shroud 220, inserter 200 is positioned in proximity with the recipient such that anterior surface 221 of shroud 200 contacts the skin of the recipient. At 806, the operator of inserter 200 can advance housing 201 towards the skin of the recipient, thereby also advancing sensor control device 102. In embodiments where shroud 220 is held in position by biasing element 215 alone, then this movement causes shroud 220 to retract. In embodiments that include lock mechanism 234, then the operator first exerts sufficient (in some embodiments predetermined) pressure in the direction of the recipient's skin to cause lock mechanism 234 to release shroud 220, at which point advancement of housing 201 towards the recipient's skin causes shroud 220 to retract.

The retraction of shroud 220 exposes sharp 211 and sensor projection 108 from anterior surface 221 of shroud 220. Because anterior surface 221 is pressed against the recipient's skin, sharp 211 pierces or punctures the exterior surface of the recipient's skin and travels into the recipient's body by a desired amount, generally equal to the remaining distance between anterior surface 221 and surface 105 of sensor control device 102. This distance can be set such that sensor projection 108 is placed subcutaneously in contact with the ISF and/or blood, or such that sensor projection 108 (and optionally sharp 211) do not exceed the depth of the dermal layer (i.e., do not pass out of the dermal layer into deeper tissue). The retraction of shroud 220 can also cause biasing element 215 to compress.

At 808, continued advancement of housing 201 towards the recipient's skin causes shroud 220 to continue to retract and, upon the exertion of sufficient (and in some embodiments predetermined) pressure then lock mechanism 254 is released. The release of lock mechanism 254 can release sharp body 205 from its secured position, and expansive force exerted by biasing mechanism 215 causes sharp body 205 to retract at 810, thereby removing sharp 211 from the body of the recipient.

At 812, if any distance remains between anterior surface 221 of shroud 220 and anterior surface 105 of sensor control device 102, then housing 201 can be advanced until surfaces 221 and 105 are at least flush. At 814, adequate pressure is exerted to secure adhesive layer 105 of sensor control device 102 to the recipient's skin. In other embodiments, alternative or additional techniques to secure sensor control device 102 can be performed. At 816, all or part of inserter 200 can be optionally removed. At 818, sensor control device 102 can be used to monitor the analyte level of the recipient, and transmit its collected data to another electronic device such as reader 120.

Embodiments of In Vivo Monitoring Systems

For purpose of illustration, and not limitation, the embodiments of inserter 200 and sensor control device 102 described herein may be used in connection with the example analyte monitoring system 100 previously described with respect to FIG. 1, which depicts an example in vivo analyte monitoring system 100 with which any and/or all of the embodiments described herein can be used. System 100 can have a sensor control device 102 and a reader device 120 that communicate with each other over a local communication path (or link) 140, which can be wired or wireless, and uni-directional or bi-directional. In embodiments where local communication path 140 is wireless, any near field communication (NFC) protocol, RFID protocol, Bluetooth or Bluetooth Low Energy protocol, Wi-Fi protocol, proprietary protocol, or the like can be used, including those communication protocols in existence as of the date of this filing or their later developed variants.

Reader device 120 can be a purpose specific device dedicated for use with analyte monitoring systems. Reader device 120 can also be a mobile communication device such as, for example, a Wi-Fi or internet enabled smartphone, tablet, or personal digital assistant (PDA). Reader device 120 can also be configured as a mobile smart wearable electronics assembly, such as an optical assembly that is worn over or adjacent to the user's eye (e.g., a smart glass or smart glasses, such as GOOGLE GLASSES). Other examples of wearable electronics include devices that are worn around or in the proximity of the user's wrist (e.g., a watch, etc.), neck (e.g., a necklace, etc.), head (e.g., a headband, hat, etc.), chest, or the like.

Reader device 120 is also capable of wired, wireless, or combined communication, either bidirectional or unidirectional, with either or all of: drug delivery device 160 over communication path (or link) 143, a local computer system 170 over communication path (or link) 141, and with a network 190 over communication path (or link) 142. The same wireless protocols described for link 140 can likewise be used for all or part of links 141, 142, and 143.

Reader device 120 can communicate with any number of entities through network 190, which can be part of a telecommunications network, such as a Wi-Fi network, a local area network (LAN), a wide area network (WAN), the internet, or other data network for uni-directional or bi-directional communication. A trusted computer system 180 can be accessed through network 190. In an alternative embodiment, communication paths 141 and 142 can be the same path which can include the network 190 and/or additional networks.

Variants of devices 102 and 120, as well as other components of an in vivo-based analyte monitoring system that are suitable for use with the system, device, and method embodiments set forth herein, are described in US Patent Application Publ. No. 2011/0213225 (the '225 Publication), which is incorporated by reference herein in its entirety for all purposes.

Sensor control device 102 can include a housing 103 containing in vivo analyte monitoring circuitry and a power source (not shown). The in vivo analyte monitoring circuitry can be electrically coupled with an analyte sensor 104 that can extend through an adhesive patch 105 and project away from housing 103. Adhesive patch 105 contains an adhesive layer (not shown) for attachment to a skin surface of the body of the user. Other forms of body attachment to the body may be used, in addition to or instead of adhesive.

Sensor 104 is adapted to be at least partially inserted into the body of the user, where it can make fluid contact with that user's body fluid (e.g., interstitial fluid (ISF), dermal fluid, or blood) and be used, along with the in vivo analyte monitoring circuitry, to measure analyte-related data of the user. Generally, sensor control device 102 and its components can be applied to the body with inserter 200 in one or more steps as described herein.

After activation, sensor control device 102 can wirelessly communicate the collected analyte data (such as, for example, data corresponding to monitored analyte level and/or monitored temperature data, and/or stored historical analyte related data) to reader device 120 where, in certain embodiments, it can be algorithmically processed into data representative of the analyte level of the user and then displayed to the user and/or otherwise incorporated into a diabetes monitoring regime.

Various embodiments disclosed herein relate to reader device 120, which can have a user interface including one or more of a display 122, keyboard, optional user interface component 121, and the like. Here, display 122 can output information to the user and/or accept an input from the user (e.g., if configured as a touch screen). Reader device 120 can include one or more optional user interface components 121, such as a button, actuator, touch sensitive switch, capacitive switch, pressure sensitive switch, jog wheel or the like. Reader device 120 can also include one or more data communication ports 123 for wired data communication with external devices such as local computer system 170. Reader device 120 may also include an integrated or attachable in vitro meter, including an in vitro test strip port (not shown) to receive an in vitro analyte test strip for performing in vitro blood analyte measurements.

Drug delivery device 160 is capable of injecting or infusing a drug, such as but not limited to insulin, into the body of the individual wearing sensor control device 102. Like reader device 120, drug delivery device 160 can include processing circuitry, non-transitory memory containing instructions executable by the processing circuitry, wireless or wired communication circuitry, and a user interface including one or more of a display, touchscreen, keyboard, an input button or instrument, and the like. Drug delivery device 160 can include a drug reservoir, a pump, an infusion tube, and an infusion cannula configured for at least partial implantation into the user's body. The pump can deliver insulin from the reservoir, through the tube, and then through the cannula into the user's body. Drug delivery device 160 can include instructions, executable by the processor, to control the pump and the amount of insulin delivered. These instructions can also cause calculation of insulin delivery amounts and durations (e.g., a bolus infusion and/or a basal infusion profile) based on analyte level measurements obtained directly or indirectly from sensor control device 102. The instructions can start drug delivery, stop drug delivery, increase or decrease the drug dosage, or modify a basal profile or a bolus dosage administered to the user. Embodiments of system 100 that include a drug delivery device 160 can be configured to operate as a semi-closed loop system or a fully closed loop system (sometimes referred to as an artificial pancreas).

Computer system 170 may be a personal or laptop computer, a tablet, or other suitable data processing device. Computer 170 can be either local (e.g., accessible via a direct wired connection such as USB) or remote to reader device 120 and can be (or include) software for data management and analysis and communication with the components in analyte monitoring system 100. Operation and use of computer 170 is further described in the '225 Publication incorporated herein by reference. Analyte monitoring system 100 can also be configured to operate with a data processing module (not shown), also as described in the incorporated '225 Publication.

Trusted computer system 180 can be used to perform authentication of sensor control device 102 and/or reader device 120, used to store confidential data received from devices 102 and/or 120, used to output confidential data to devices 102 and/or 120, or otherwise configured. Trusted computer system 180 can include one or more computers, servers, networks, databases, and the like. Trusted computer system 180 can be within the possession of the manufacturer or distributor of sensor control device 102, either physically or virtually through a secured connection, or can be maintained and operated by a different party (e.g., a third party).

The processing of data and the execution of software within system 100 can be performed by one or more processors of reader device 120, computer system 170, and/or sensor control device 102. For example, raw data measured by sensor 104 can be algorithmically processed into a value that represents the analyte level and that is readily suitable for display to the user, and this can occur in sensor control device 102, reader device 120, or computer system 170. This and any other information derived from the raw data can be displayed in any of the manners described above (with respect to display 122) on any display residing on any of sensor control device 102, reader device 120, or computer system 170. The information may be utilized by the user to determine any necessary corrective actions to ensure the analyte level remains within an acceptable and/or clinically safe range.

Figure 9:
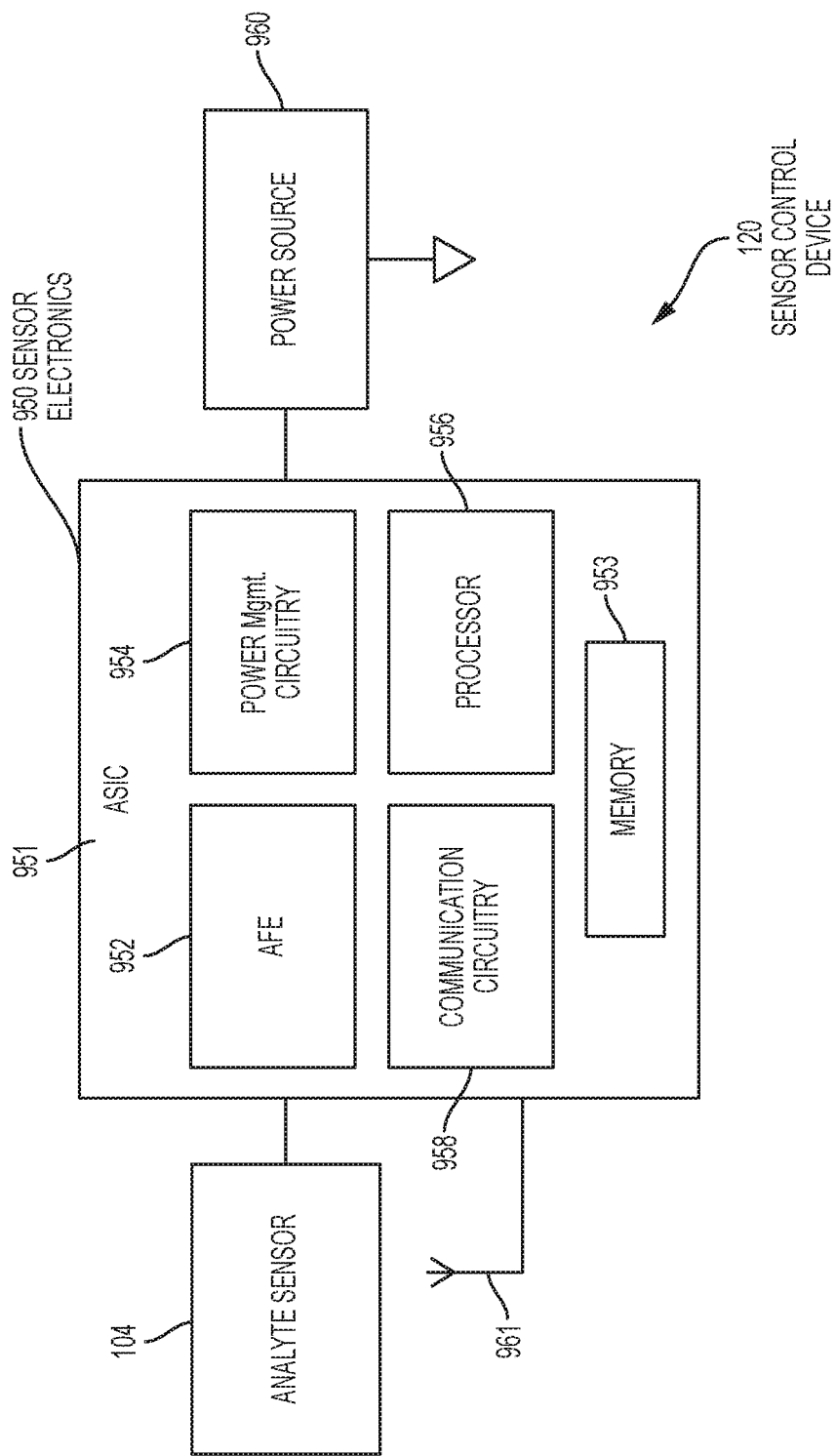
FIG. 9 is a block diagram depicting an example embodiment of a sensor control device.

FIG. 9 is a block schematic diagram depicting an example embodiment of sensor control device 102 having analyte sensor 104 and sensor electronics 950 (including analyte monitoring circuitry). Although any number of chips can be used, here the majority of the sensor electronics 950 are incorporated on a single semiconductor chip 951 that can be, e.g., a custom application specific integrated circuit (ASIC). Shown within ASIC 951 are several high-level functional units, including an analog front end (AFE) 952, power management circuitry 954, processor 956, and communication circuitry 958 (which can be implemented as a transmitter, receiver, transceiver, passive circuit, or otherwise according to the communication protocol). In this embodiment shown here, both AFE 952 and processor 956 are used as analyte monitoring circuitry, but in other embodiments either circuit can perform the analyte monitoring function. Processor 956 can include one or more processors, microprocessors, controllers, and/or microcontrollers.

A non-transitory memory 953 is also included within ASIC 951 and can be shared by the various functional units present within ASIC 951, or can be distributed amongst two or more of them. Memory 953 can be volatile and/or non-volatile memory. In this embodiment, ASIC 951 is coupled with power source 960, which can be a coin cell battery, or the like. AFE 952 interfaces with in vivo analyte sensor 104 and receives measurement data therefrom and outputs the data to processor 956 in digital form, which in turn processes the data to arrive at the end-result analyte discrete and trend values, etc. This data can then be provided to communication circuitry 958 for sending, by way of antenna 961, to reader device 120 (not shown) where further processing can be performed by, e.g., the sensor interface application. It should be noted that the functional components of ASIC 951 can also be distributed amongst two or more discrete semiconductor chips.

Performance of the data processing functions within the electronics of the sensor control device 102 provides the flexibility for system 100 to schedule communication from sensor control device 102 to reader device 120, which in turn limits the number of unnecessary communications and can provide further power savings at sensor control device 102.

Information may be communicated from sensor control device 102 to reader device 120 automatically and/or continuously when the analyte information is available, or may not be communicated automatically and/or continuously, but rather stored or logged in a memory of sensor control device 102, e.g., for later output.

Data can be sent from sensor control device 102 to reader device 120 at the initiative of either sensor control device 102 or reader device 120. For example, in many example embodiments sensor control device 102 can communicate data periodically in an unprompted or broadcast-type fashion, such that an eligible reader device 120, if in range and in a listening state, can receive the communicated data (e.g., sensed analyte data). This is at the initiative of sensor control device 102 because reader device 120 does not have to send a request or other transmission that first prompts sensor control device 102 to communicate. Broadcasts can be performed, for example, using an active Wi-Fi, Bluetooth, or BTLE connection. The broadcasts can occur according to a schedule that is programmed within device 102 (e.g., about every 1 minute, about every 5 minutes, about every 10 minutes, or the like). Broadcasts can also occur in a random or pseudorandom fashion, such as whenever sensor control device 102 detects a change in the sensed analyte data. Further, broadcasts can occur in a repeated fashion regardless of whether each broadcast is actually received by a reader device 120.

System 100 can also be configured such that reader device 120 sends a transmission that prompts sensor control device 102 to communicate its data to reader device 120. This is generally referred to as "on-demand" data transfer. An on-demand data transfer can be initiated based on a schedule stored in the memory of reader device 120, or at the behest of the user via a user interface of reader device 120. For example, if the user wants to check his or her analyte level, the user could perform a scan of sensor control device 102 using an NFC, Bluetooth, BTLE, or Wi-Fi connection. Data exchange can be accomplished using broadcasts only, on-demand transfers only, or any combination thereof.

Accordingly, once a sensor control device 102 is placed on the body so that at least a portion of sensor 104 is in contact with the bodily fluid and electrically coupled to the electronics within device 102, sensor derived analyte information may be communicated in on-demand or unprompted (broadcast) fashion from the sensor control device 102 to a reader device 120. On-demand transfer can occur by first powering on reader device 120 (or it may be continually powered) and executing a software algorithm stored in and accessed from a memory of reader device 120 to generate one or more requests, commands, control signals, or data packets to send to sensor control device 102. The software algorithm executed under, for example, the control of processing hardware 206 of reader device 120 may include routines to detect the position of the sensor control device 102 relative to reader device 120 to initiate the transmission of the generated request command, control signal and/or data packet.

It should be noted that all features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. It is explicitly acknowledged that express recitation of every possible combination and substitution is overly burdensome, especially given that the permissibility of each and every such combination and substitution will be readily recognized by those of ordinary skill in the art.

To the extent the embodiments disclosed herein include or operate in association with memory, storage, and/or computer readable media, then that memory, storage, and/or computer readable media are non-transitory. Accordingly, to the extent that memory, storage, and/or computer readable media are covered by one or more claims, then that memory, storage, and/or computer readable media is only non-transitory.

In many instances entities are described herein as being coupled to other entities. It should be understood that the terms "coupled" and "connected" (or any of their forms) are used interchangeably herein and, in both cases, are generic to the direct coupling of two entities and the indirect coupling of two entities. Where entities are shown as being directly coupled together, or described as coupled together without description of any intervening entity, it should be understood that those entities can be indirectly coupled together as well unless the context clearly dictates otherwise.

The subject matter described herein and in the accompanying figures is done so with sufficient detail and clarity to permit the inclusion of claims, at any time, in means-plus-function format pursuant to 35 U.S.C. section 112, part (f). However, a claim is to be interpreted as invoking this means-plus-function format only if the phrase "means for" is explicitly recited in that claim.

As used herein and in the appended claims, the singular forms "a", "an", and "the" include plural referents unless the context clearly dictates otherwise.

While the embodiments are susceptible to various modifications and alternative forms, specific examples thereof have been shown in the drawings and are herein described in detail. These embodiments are not to be limited to the particular form disclosed, but to the contrary, these embodiments are to cover all modifications, equivalents, and alternatives falling within the spirit of the disclosure. Furthermore, any features, functions, steps, or elements of the embodiments may be recited in or added to the claims, as well as negative limitations that define the scope of the claims by features, functions, steps, or elements that are not within that scope.

What is claimed is:

1. A method for inserting an analyte sensor into a human body with an inserter, the inserter comprising a posterior housing, a sensor control device coupled with the housing, the analyte sensor, a sharp, and a shroud, the method comprising:
   placing an anterior surface of the shroud against a recipient's skin, wherein the shroud, the analyte sensor, and the sharp are extended with respect to an anterior surface of the sensor control device, wherein the shroud covers the analyte sensor and the sharp, and wherein the shroud is held extended with respect to the anterior surface of the sensor control device by a first lock mechanism comprising a structure on the shroud that locks with a structure on the sensor control device;
   advancing the sensor control device towards the recipient's skin such that the shroud retracts with respect to the sensor control device and the sharp and analyte sensor are inserted into the recipient's body; and
   withdrawing the sharp while leaving the analyte sensor within the recipient's body.

2. The method of claim 1, wherein the sharp and analyte sensor are inserted into the recipient's body through an aperture in the shroud.

3. The method of claim 1, wherein the structure on the shroud is a detent and the structure on the sensor control device is a recess.

4. The method of claim 1, wherein the inserter further comprises a biasing element, the method further comprising automatically withdrawing the sharp from the recipient's body with a force applied by the biasing element.

5. The method of claim 4, wherein the sharp is coupled with a posterior mount, the method comprising automatically withdrawing the sharp from the recipient's body with the force applied by the biasing element against the posterior mount.

6. The method of claim 5, wherein the biasing element contacts a base of the shroud and a surface on the posterior mount, and is adapted to apply the force therebetween.

7. The method of claim 5, wherein the biasing element is in a uncompressed state when the shroud is extended, the method further comprising advancing the sensor control device towards the recipient's skin such that the shroud retracts with respect to the sensor control device and the biasing element transitions from the uncompressed state to a compressed state.

8. The method of claim 7, further comprising releasing a second lock mechanism wherein, upon release, the biasing element decompresses from the compressed state and causes withdrawal of the sharp from the recipient's body.

9. The method of claim 8, wherein the second lock mechanism comprises an elastic arm coupled with the housing and adapted to releasably hold the posterior mount in position with respect to the sensor control device.

10. The method of claim 9, wherein retraction of the shroud causes a release surface of the shroud to deflect the elastic arm and thereby release the second lock mechanism.

11. The method of claim 7, wherein the inserter further comprises two elastic arms coupled with the housing and adapted to releasably hold the posterior mount in position with respect to the sensor control device.

12. The method of claim 11, wherein upon placement of the anterior surface of the shroud against the recipient's skin, the two elastic arms are holding the posterior mount in position with respect to the sensor control device and, wherein retraction of the shroud causes a release surface of the shroud to deflect the two elastic arms and thereby release the posterior mount from the elastic arms.

13. The method of claim 12, wherein after release of the posterior mount from the elastic arms, the biasing element decompresses from the compressed state and causes withdrawal of the sharp from the recipient's body.

14. The method of claim 1, further comprising adhesively coupling an anterior surface of the sensor control device to the recipient's skin.

15. The method of claim 14, further comprising withdrawing the inserter such that the sensor control device is separated from the inserter and the sensor control device remains adhesively coupled to the recipient's skin with the analyte sensor at least partially implanted within the recipient's body.

16. The method of claim 15, wherein, after withdrawal of the inserter, an electrode on the analyte sensor is in contact with a fluid of the recipient and capable of measuring a level of an analyte in the fluid, wherein the fluid is only interstitial fluid or only dermal fluid.

17. The method of claim 16, wherein the analyte is glucose.

18. The method of claim 1, wherein the sensor control device is coupled with the housing of the inserter and advancing the sensor control device towards the recipient's skin comprises grasping the housing of the inserter and advancing the housing towards the recipient's skin.

* * * * *